United States Patent [19]

Phillips et al.

[11] Patent Number: 5,668,137
[45] Date of Patent: Sep. 16, 1997

[54] N-HETEROCYCLIC SULFONAMIDES HAVING ENDOTHELIN RECEPTOR ACTIVITY

[75] Inventors: Paul John Phillips, Congleton; Peter Grahame Ballard, Stockport; Robert Hugh Bradbury, Wilmslow; Roger James, Congleton, all of United Kingdom

[73] Assignee: Zeneca Ltd., London, England

[21] Appl. No.: 667,131

[22] Filed: Jun. 20, 1996

[30] Foreign Application Priority Data

Jun. 22, 1995 [GB] United Kingdom ............ 9512697

[51] Int. Cl.⁶ .................... C07D 241/00; A61K 31/54
[52] U.S. Cl. ................................ 514/255; 544/336
[58] Field of Search ..................... 544/336; 514/255

[56] References Cited

U.S. PATENT DOCUMENTS

| | | | |
|---|---|---|---|
| 5,270,313 | 12/1993 | Burri et al. | 514/252 |
| 5,292,740 | 3/1994 | Burri et al. | 514/256 |
| 5,397,798 | 3/1995 | Fitch et al. | 514/399 |
| 5,420,129 | 5/1995 | Breu et al. | 514/252 |
| 5,464,853 | 11/1995 | Chan et al. | 514/378 |

FOREIGN PATENT DOCUMENTS

| | | |
|---|---|---|
| 510526 | 10/1992 | European Pat. Off. . |
| 526708 | 2/1993 | European Pat. Off. . |
| 558258 | 9/1993 | European Pat. Off. . |
| 569193 | 11/1993 | European Pat. Off. . |
| 601386 | 6/1994 | European Pat. Off. . |
| 640596 | 3/1995 | European Pat. Off. . |
| 682016 | 11/1995 | European Pat. Off. . |
| 0 626 174 | 1/1996 | European Pat. Off. . |
| 0 702 012 | 3/1996 | European Pat. Off. . |
| 61-257960 | 11/1986 | Japan . |
| 2 295 616 | 6/1996 | United Kingdom . |
| WO9009787 | 9/1990 | WIPO . |
| WO9427979 | 12/1994 | WIPO . |
| WO9526957 | 10/1995 | WIPO . |

OTHER PUBLICATIONS

R.D. Desai et al., "Studies in Sulphonamides: Part II. Preparation of N¹-Heterocyclic Substituted Sulphonamides from Alpha-naphthylamine and Evaluation of their Antibacterial Properties", *Jour. Indian Chem. Soc.*, pp. 115–118, vol. 46, No. 2, 1969.

R.D. Desai et al., "Studies in Sulphonamides: Part IV. Some N⁶-Heterocyclic Sulphonamides from 2-Naphthylamine as possible Antibacterial Agents", *J. Indian Chem. Soc.*, pp. 411–414, vol. 46, No. 5, 1969.

P. Mamalis et al., "142. Some Heterocyclic N–Oxides", *J. Chem. Soc.*, pp. 703–705, 1950.

Chemical Abstracts, vol. 84, No. 15, 1976, 84:100672y.

Chemical Abstracts, vol. 100, No. 15, 1984, 100:131420t.

Chemical Abstracts, vol. 106, No. 17, 1987, 106:133792p (corresponds to JP61257960).

Himel et al., "Fluorescent Analogs of Insecticides and Synergists. Synthesis and Reactions of Active–Site–Directed Fluorescent Probes", *Journal Agr. Food Chem.*, vol. 19, No. 6, 1971, pp. 1175–1180.

Shigehara et al., "Preparation of Pyridine Derivatives and their Salts as Phospholipase $A_2$ Inhibitors", *Chemical Abstracts*, vol. 122, No. 25, 1995, 122:314455g.

STN Printout identifying compounds disclosed in PCT 90–009787 and Japan 61–257960.

The Discovery of Sulfonamide Endothelin Antagonists and the Development of the Orally Active $ET_A$ antagonist 5–(Dimethylamino)–N–(3, 4–dimethyl–5–isoxazolyl)–1–naphthalenesul fonamide, *Journal of Medicinal Chemistry*, Feb. 4, 1994, vol. 37, No. 3, pp. 329–331.

Identification of a New Class of $ET_A$ Selective Endothelin Antagonists by Pharmacophore Directed Screening, *Biochemical and Biophysical Research Communications*, May 30, 1994, vol. 201, No. 1, pp. 228–234.

Pharmacological Characterization of Bosentan, a New Potent Orally Active Nonpeptide Endothelin Receptor Antagonist, *Journal Pharmacol. Exp. Therap.*, 1994, 270, 228–235.

Pages copied from a book of abstracts provided in an International Business Communications Conference entitled "Endothelin Inhibitors—Advances in Therapeutic Application and Development", Philadelphia, PA, Jun. 9–10, 1994, 33 pages.

*Primary Examiner*—Matthew V. Grumbling
*Assistant Examiner*—Michael Bucknum
*Attorney, Agent, or Firm*—Robert J. Harris; Patrick H. Higgins

[57] ABSTRACT

The invention concerns pharmaceutically useful compounds of the formula I, in which $R^1$, $R^2$, $R^3$, n, m and Het have any of the meanings defined herein, and their pharmaceutically-acceptable salts, and pharmaceutical compositions containing them. The novel compounds possess endothelin receptor antagonist activity and are useful, for example, in the treatment of diseases or medical conditions in which elevated or abnormal levels of endothelin play a significant causative role. The invention further concerns processess for the manufacture of the novel compounds and the use of the compounds in medical treatment.

9 Claims, No Drawings

N-HETEROCYCLIC SULFONAMIDES HAVING ENDOTHELIN RECEPTOR ACTIVITY

The present invention relates to novel nitrogen compounds and, more particulary, to novel N-heterocyclyl sulphonamides, and pharmaceutically-acceptable salts thereof, which possess endothelin receptor antagonist activity. These compounds are of value whenever such antagonist activity is desired, such as for research tools within pharmacological, diagnostic and related studies or in the treatment of diseases or medical conditions including, but not limited to, hypertension, pulmonary hypertension, cardiac or cerebral circulatory disease and renal disease, in warm-blooded animals (including man), in which elevated or abnormal levels of endothelin play a significant causative role. The invention also relates to pharmaceutical compositions of the novel compounds (and their salts) for use in treating said diseases or medical conditions, and to processes for the manufacture of the novel compounds. The invention further relates to the use of the novel compounds in treating one or more of the said diseases or medical conditions. A method of treating one or more of the said diseases or medical conditions using said compounds is also provided.

The endothelins are a family of endogenous 21 amino acid peptides comprising three isoforms, endothelin-1, endothelin-2 and endothelin-3. The endothelins are formed by cleavage of the $Trp^{21}$–$Val^{22}$ bond of their corresponding proendothelins by a putative endothelin converting enzyme. The endothelins are among the most potent vasoconstrictors known and have a characteristic long duration of action. They exhibit a wide range of other activities including cell proliferation and mitogenesis, extravasation and chemotaxis, and also interact with a number of other vasoactive agents. They also have direct effects on the heart. Thus the biological profile of the endothelins is consistent with a pathophysiological role in the cardiovascular system. The endothelins also have actions on other physiological systems including the airways, gastro-intestinal tract, reproductive system, kidney, liver, central nervous system, neuroendocrine system and the blood.

The endothelins am released from a range of tissue and cell sources including vascular endothelium, vascular smooth muscle, kidney, liver, uterus, airways, intestine and leukocytes. Release can be stimulated by hypoxia, shear stress, physical injury and a wide range of hormones and cytokines. Elevated endothelin levels have been found in a number of disease states in man including hypertension, pulmonary hypertension, pre-eclampsia, congestive heart failure, myocardial infarction, angina pectoris, acute and chronic renal failure, ischaemic stroke, subarachnoid haemorrhage, atherosclerosis, hypercholesterolaemia, cardiogenic and endotoxic shock, diabetes mellitus, Raynaud's disease, scleroderma, systemic sclerosis, Buerger's disease, rheumatoid arthritis, asthma, bronchitis, acute respiratory failure, liver cirrhosis, Crohn's disease, ulcerative colitis, certain cancers and after surgery.

In European patent applications, publications nos. 558258 and 569193, and in International patent appliaction, publication no. WO 94/27979, are described certain N-(isozaxolyl)sulphonamides and in European patent application, publication no.640596 are described certain N-(pyridazinyl)sulphonamides, which are referred to as endothelin receptor antagonists.

Although a number of endothelin receptor antagonists are known, there is a continuing need for alternative antagonists. The present invention is based in part on this need and on our discovery of the unexpected antagonism of the endothelin receptor by certain N-heterocyclyl sulphonamides.

According to one aspect of the invention there is provided a compound of the formula I (set our hereinafter, together with the other chemical formulae identified by Roman numerals) wherein $R^1$ is (1–6C)alkyl, (2–6C)alkenyl, (2–6C)alkynyl, (1–6C)alkoxy or (1–6C)alkythio, each of which last five groups bear a substituent selected from carboxy, (1–6C)alkoxycarbonyl, carbamoyl, N-(1–6C)alkylcarbamoyl and N,N-di(1–6C)alkylcarbamoyl;

$R^2$ is an optional substituent selected from halogeno, (1–6C)alkyl, (1–6C)alkoxy, carboxy, (1–6C)alkoxycarbonyl, carbamoyl, N-(1–6C)alkylcarbamoyl, N,N-di(1–6C)alkylcarbamoyl, cyano, amino, N-(1–6C)alkylamino and N,N-di(1–6C)alkylamino;

$R^3$ is an optional substituent selected from (1–6C)alkyl, amino(1–6C)alkyl, hydroxy(1–6C)alkyl, N-[(1–4C)alkyl]amino(1–6C)alkyl, N,N-[di(1–4C)alkyl]amino(1–6C)alkyl, carboxy(1–6C)alkyl, (1–6C)alkoxycarbonyl(1–6C)alkyl, carbamoyl (1–6C)alkyl, (1–6C)alkylcarbamoyl(1–6C)alkyl, di(1–6C)alkylcarbamoyl(1–6C)alkyl, carboxy(1–6C)alkoxy, carboxy(1–6C)alkylthio, (1–6C)alkoxycarbonyl(1–6C)alkoxy, (1–6C)alkoxycarbonyl(1–6C)alkylthio, carbamoyl(1–6C)alkoxy, (1–6C)alkylcarbamoyl(1–6C)alkoxy, di(1–6C)alkylcarbamoyl(1–6C)-alkoxy, carbamoyl(1–6C)alkylthio, (1–6C)alkylcarbamoyl(1–6C)alkylthio, di(1–6C)alkylcarbamoyl(1–6C)alkylthio, (2–6C)alkenyl, carboxy(2–6C)alkenyl, (2–6C)alkynyl, carboxy(2–6C)alkynyl, (1–6C)alkoxycarbonyl(2–6C)alkenyl, carbamoyl(2–6C)alkenyl, carbamoyl(2–6C)alkenyl, N-(1–6C)alkylcarbamoyl(2–6C)alkenyl, N,N-di(1–6C)alkylcarbonyl(2–6C)alkenyl, (1–6C)alkoxycarbonyl(2–6C)alkynyl, carbamoyl(2–6C)alkynyl, N-(1–6C)alkylcarbamoyl(2–6C) alkynyl, N,N-di(1–6C)alkylcarbamoyl(2–6C)alkynyl, halogeno (2–6C)alkyl, trifluoromethyl, trichloromethyl, tribromomethyl, (1–6C)alkoxy, dihalogeno(1–6C)alkoxy, trihalogeno(1–6C)alkoxy, (2–6C)alkenyloxy, (1–4C)alkoxy(1–6C)alkyl, (1–4C)alkylthio(1–6C)alkyl, (1–4C)alkylsulphinyl(1–6C)alkyl, (1–4C)alkylsulphonyl(1–6C)alkyl, (1–4C)alkylenedioxy, (3–6C)cycloalkyl, (3–8C)cycloalkyl(1–6C)alkyl, phenyl, phenyl(1–6C)alkyl, phenoxy, phenyl(1–6C)alkoxy, halogeno, hydroxy, mercapto, cyano, nitro, carboxy, (1–6C)alkoxycarbonyl, (2–6C)alkenyloxycarbonyl, phenyloxycarbonyl, phenyl(1–6C)alkoxycarbonyl, (1–6C)alkanoyl, benzoyl, (1–6C)alkylthio, (1–6C)alkylsulphinyl, (1–6C)alkylsulphonyl, phenylthio, phenylsulphinyl, phenylsulphonyl, (1–6C)alkanoylamino, trifluoroacetyl, trifluoroacetamido, N-[(1–4C)alkyl]trifluoroacetamido, benzamido, N-[(1–4C)alkyl]benzamido, carbamoyl, (1–4C)alkylcarbamoyl, di-(1–4C)alkylcarbamoyl, phenylcarbamoyl, sulphamoyl, N-(1–4C)alkylsulphamoyl, N,N-di(1–4C)alkylsulphamoyl, N-phenylsulphamoyl, (1–6C)alkanesulphonamido, benzenesulphonamido, ureido, 3-(1–6C)alkylureido, 3-phenylureido, thioureido, 3-(1–6C)alkylthioureido, 3-phenylthioureido and a group —NRyRz in which Ry and Rz are independently selected from hydrogen, (1–6C)alkyl, phenyl(1–4C)alkyl and (1–6C)alkyl bearing a carboxy, (1–6C)alkoxycarbonyl, carbamoyl, (1–6C)alkylcarbamoyl or di(1–6C)alkylcarbamoyl group, or the group —NRyRz taken together complete a 1-pyrrolidinyl, 2-oxo-1-pyrrolidinyl, 1-piperidinyl or 2-oxo-1-piperidinyl ring;

Het is a heterocyclic ring selected from the groups of partial structural formulae IIa, IIb, IIc, IId and IIe set out hereinafter wherein Ra, Rc and Re are individually selected from hydrogen, halogeno, (1–4C)alkyl, (1–4C)alkoxy and trifluoromethoxy; Rb is selected from hydrogen, halogeno, (1–4C)alkyl, methoxy, ethoxy, trifluoromethyl and ethynyl; Rd and Rf are individually selected from halogeno, (1–4C)alkyl, methoxy, ethoxy, trifluoromethyl and ethynyl; Rg is selected from methyl and bromo; Rh is methoxy or ethoxy;

m is zero, 1, 2 or 3;

n is zero, 1, 2 or 3; and wherein any of said phenyl or benzene moieties of $R^3$ may be unsubstituted or bear one or two substituents independently selected from (1–4C)alkyl, (1–4C)alkoxy, halogeno, cyano and trifluoromethyl; or a pharmaceutically-acceptable salt thereof.

It will be appreciated that, depending on the nature of the substituents, certain of the formula I compounds may possess one or more chiral centres and may be isolated in one or more racemic or optically active forms. It is to be understood that the present invention concerns any form of such a compound of formula I which possesses the aforementioned useful pharmacological properties, it being well known how to make optically active forms, for example by synthesis from suitable chiral intermediates or by resolution, and how to determine their pharmacological properties, for example by use of the tests described hereinafter.

It will also be appreciated that a compound of formula I may exhibit polymorphism, that a compound of formula I may form a solvate and that a compound of formula I may exist in more than one tautomeric form. It is to be understood that the present invention also concerns any polymorphic form, any tautomer or any solvate, or any mixture thereof, which possesses endothelin receptor antagonist activity.

It will further be appreciated that a compound of the formula I may be chemically modified such that in vivo it is converted into a parent compound of the formula I (for example, by hydrolytic, oxidative or enzymatic cleavage). Such chemically modified compounds are commonly referred to as prodrugs and may be, for example, metabolically labile ester or amide derivatives of a parent compound having a carboxylic acid group (or a metabolically labile ester of a parent compound having an hydroxy group). It is to be understood that the present invention also concerns any such prodrugs, including metabolically labile ester or amide derivatives of compounds of the formula I.

It is further to be understood that generic terms such as "alkyl", "alkenyl", "alkynyl", "alkoxy", "alkylthio" and "alkoxycarbonyl" include both straight and branched chain variants when the carbon numbers permit.

However, when a particular radical such as "propyl" is given, it is specific to the straight chain variant, branched chain variants such as "isopropyl" being specifically named when intended. The same convention applies to other radicals.

It is further to be appreciated that in those compounds in which there is more than one substituent $R^2$ or $R^3$ present (i.e. when m or n is 2 or 3), the value for each $R^2$ or $R^3$ may be the same or different.

Particular values for $R^1$, $R^2$ and $R^3$ where appropriate include, by way of example, for (1–6C)alkyl: (1–4C)alkyl, such as methyl, ethyl, propyl, isopropyl and sec-butyl; for amino(1–6C)alkyl: amino (1–4C)alkyl, such as aminomethyl and 2-aminoethyl; for hydroxy(1–6C)alkyl: hydroxy(1–4C)alkyl, such as hydroxymethyl, 1-hydroxyethyl and 2-hydroxyethyl;

for N-[(1–4C)alkyl]amino(1–6C)alkyl: N-[(1–2C)alkylamino(1–4C)alkyl, such as methylaminomethyl and 2-(methylamino)ethyl;

for N,N-[di(1–4C)alkyl]amino(1–6C)alkyl: N,N-[di(1–2C)alkyl]amino(1–4C)alkyl, such as dimethylaminomethyl and 2-(dimethylamino)ethyl;

for carboxy(1–6C)alkyl: carboxy(1–4C)alkyl, such as carboxymethyl, 1-carboxyethyl, 2-carboxyethyl and 2-carboxypropyl;

for (1–6C)alkoxycarbonyl(1–6C)alkyl: (1–4C)alkoxycarbonyl(1–4C)alkyl, such as methoxycarbonylmethyl, ethoxycarbonylmethyl, 1-(methoxycarbonyl)ethyl, 2-(methoxycarbonyl)ethyl, 1-(ethoxycarbonyl)ethyl, 2-(ethoxycarbonyl)ethyl, 2-(methoxycarbonyl)propyl and 2-(ethoxycarbonyl)propyl;

for carboxy(1–6C)alkoxy: carboxy(1–4C)alkoxy, such as carboxymethoxy, 1-carboxyethoxy, 2-carboxyethoxy and 2-carboxypropoxy;

for carboxy(1–6C)alkylthio: carboxy(1–4C)alkylthio, such as carboxymethylthio, 1-carboxyethylthio, 2-carboxyethylthio and 2-carboxypropylthio;

for (1–6C)alkoxycarbonyl(1–6C)alkoxy: (1–4C)alkoxycarbonyl(1–4C)alkoxy, such as methoxycarbonylmethoxy, ethoxycarbonylmethoxy, 1-(methoxycarbonyl)ethoxy, 1-(ethoxycarbonyl)ethoxy, 2-(methoxycarbonyl)ethoxy, 2-(ethoxycarbonyl)ethoxy, 2-(methoxycarbonyl)propoxy and 2-(ethoxycarbonyl)propoxy;

for (1–6C)alkoxycarbonyl(1–6C)alkylthio: (1–4C)alkoxycarbonyl(1–4C)alkylthio, such as (methoxycarbonyl)methylthio, ethoxycarbonylmethylthio, 1-(methoxycarbonyl)ethylthio, 1-(ethoxycarbonyl)ethylthio, 2-(methoxycarbonyl)ethylthio, 2-(ethoxycarbonyl)ethylthio, 2-(methoxycarbonyl)propylthio, and 2-(ethoxycarbonyl)propylthio;

for (2–6C)alkenyl: (2–4C)alkenyl, such as vinyl, allyl, 1-propenyl and 2-butenyl;

for carbamoyl(1–6C)alkyl: carbamoyl(1–4C)alkyl, such as carbamoylmethyl, 1-carbamoylethyl, 2-carbamoylethyl and 2-carbamoylpropyl;

for (1–6C)alkylcarbamoyl(1–6C)alkyl: (1–4C)alkylcarbamoyl(1–4C)alkyl, such as (N-methylcarbamoyl)methyl, (N-ethylcarbamoyl)methyl, 1-(N-methylcarbamoyl)ethyl, 2-(N-methylcarbamoyl)ethyl, 1-(N-ethylcarbamoyl)ethyl, 2-(N-ethylcarbamoyl)ethyl, 2-(N-methylcarbamoyl)ethyl, 1-(N-ethylcarbamoyl)ethyl, 2-(N-ethylcarbamoyl)ethyl, 2-(N-methylcarbamoyl)propyl and 2-(N-ethylcarbamoyl)propyl;

for di(1–6C)alkylcarbamoyl(1–6C)alkyl: di(1–4C)alkylcarbamoyl(1–4C)alkyl, such as (N,N-dimethylcarbamoyl)methyl, (N,N-diethylcarbamoyl)methyl, 1-(N,N-dimethylcarbamoyl)ethyl, 2-(N,N-dimethylcarbamoyl)ethyl, 1-(N,N-diethylcarbamoyl)ethyl, 2-(N,N-diethylcarbamoyl)ethyl, 2-(N, N-dimethylcarbamoyl)propyl and 2-(N,N-diethylcarbamoyl)propyl;

for carbamoyl(1–6C)alkoxy: carbamoyl(1–4C)alkoxy, such as carbamoylmethoxy, 1-carbamoylethoxy, 2-carbamoylethoxy and 2-carbamoylpropoxy;

for (1–6C)alkylcarbamoyl(1–6C)alkoxy: (1–4C)carbamoyl (1–4C)alkoxy, such as (N-methylcarbamoyl)methoxy, (N-ethylcarbamoyl)methoxy, 1-(N-methylcarbamoyl)ethoxy, 2-(N-methylcarbamoyl)ethoxy, 1-(N-ethylcarbamoyl)ethoxy, 2-(N-ethylcarbamoyl)ethoxy, 2-(N-methylcarbamoyl)propoxy and 2-(N-ethylcarbamoyl)propoxy;

for di(1–6C)alkylcarbamoyl(1–6C)alkoxy: di(1–4C)alkyl (1–4C)alkoxy, such as (N,N-dimethylcarbamoyl)methoxy, (N,N-diethylcarbamoyl)methoxy, 1-(N,N-dimethylcarbamoyl)ethoxy, 2-(N,N-dimethylcarbamoyl)ethoxy, 1-(N,N-diethylcarbamoyl)ethoxy, 2-(N,N-diethylcarbamoyl)ethoxy, 2-(N,N-dimethylcarbamoyl)propoxy and 2-(N,N-diethylcarbamoyl)propoxy;

for carbamoyl(1–6C)alkylthio: carbamoyl(1–6C)alkylthio, such as carbamoylmethylthio, 1-carbamoylethylthio, 2-carbamoylethylthio and 2-carbamoylpropylthio;

for (1–6C)alkylcarbamoyl(1–6C)alkylthio: (1–4C) alkylcarbamoyl(1–4C)alkylthio, such as (N-methylcarbamoyl)methylthio, (N-ethylcarbamoyl)methylthio,( N-ethylcarbamoyl)methylthio, 1-(N-methylcarbamoyl)ethylthio, 2-(N-methylcarbamoyl)ethylthio, 1-(N-ethylcarbamoyl)ethylthio, 2-(N-ethylcarbamoyl)ethylthio, 2-(N-methylcarbamoyl)propylthio and 2-(N-ethylcarbamoyl)propylthio;

for di(1–6C)alkylcarbamoyl(1–6C)alkylthio: di(1–4C) alkylcarbamoyl(1–4C)alkylthio, such as (N,N-dimethylcarbamoyl)methylthio, (N,N-diethylcarbamoyl)methylthio, 1-(N,N-dimethylcarbamoyl)ethylthio, 2-(N,N-dimethylcarbamoyl)ethylthio, 1-(N,N-diethylcarbamoyl)ethylthio, 2-(N,N-diethylcarbamoyl)ethylthio, 2-(N,N-dimethylcarbamoyl)propylthio and 2-(N,N-diethylcarbamoyl)propylthio;

for carboxy(2–6C)alkenyl: carboxy(2–4C)alkenyl, such as 2-carboxyethenyl, 3-carboxy-1-propenyl and 4-carboxy-2-butenyl;

for carboxy(2–6C)alkynyl: carboxy(2–4C)alkynyl, such as carboxyethynyl, 3-carboxy-1-propynyl and 4-carboxy-2-butynyl;

for (2–6C)alkynyl: (2–4C)alkynyl, such as ethynyl, 1-propynyl, 2-propynyl and 1-butynyl;

for (1–6C)alkoxycarbonyl(2–6C)alkenyl: (1–4C) alkoxycarbonyl(2–4C)alkenyl, such as 2-methoxycarbonylethenyl, 2-ethoxycarbonylethenyl, 3-methoxycarbonyl-1-propenyl, 3-ethoxycarbonyl-1-propenyl, 4-methoxycarbonyl-2-butenyl and 4-ethoxycarbonyl-2-butenyl;

for carbamoyl(2–6C)alkenyl: carbamoyl(2–4C)alkenyl, such as 2-carbamoylethenyl, 3-carbamoyl-1-propenyl and 4-carbamoyl-2-butenyl;

for N-(1–6C)alkylcarbamoyl(2–6C)alkenyl: N-(1–4C)alkylcarbamoyl(2–4C)-alkenyl, such as 2-(N-methylcarbamoyl)ethenyl, 2-(N-ethylcarbamoyl)ethenyl, 3-(N-methylcarbamoyl)-1-propenyl, 3-(N-ethylcarbamoyl)-1-propenyl, 4-(N-methylcarbamoyl)-2-butenyl and 4-(N-ethylcarbamoyl)-2-butenyl;

for N,N-di(1–6C)alkylcarbamoyl(2–6C)alkenyl: N,N-di(1–4C)alkylcarbamoyl(2–4C)alkenyl, such as 2-(N,N-dimethylcarbamoyl)ethenyl, 2-(N,N-diethylcarbamoyl)ethyl, 3-(N,N-dimethylcarbamoyl)-1-propenyl, 3-(N,N-diethylcarbamoyl)-2-butenyl, 4-(N,N-dimethylcarbamoyl)-2-butenyl and 4-(N,N-diethylcarbamoyl)-2-butenyl;

for (1–6C)alkoxycarbonyl(2–6C)alkynyl: (1–4C) alkoxycarbonyl(2–4C)alkynyl, such as methoxycarbonylethynyl, ethoxycarbonylethynyl, 3-methoxycarbonyl-1-propynyl, 3-ethoxycarbonyl-1-propynyl, 4-methoxycarbonyl-2-butynyl and 4-ethoxycarbonyl-2-butynyl;

for carbamoyl (2–6C)alkynyl: carbamoyl(2–4C)alkynyl such as carbamoylethynyl, 3-carbamoyl-1-propynyl and 4-carbamoyl-2-butynyl;

for N-(1–6C)alkylcarbamoyl(2–6C)alkynyl: N-(1–4C)alkylcarbamoyl(2–4C) alkynyl, such as N-methylcarbamoylethynyl, N-ethylcarbamoylethynyl, 3-(N-methylcarbamoyl)-1-propynyl, 3-(N-ethylcarbamoyl)-1-propynyl, 4-(N-methylcarbamoyl)-2-butynyl and 4-(N-ethylcarbamoyl)-2-butynyl;

for N,N-di(1–6C)alkylcarbamoyl(2–6C)alkynyl: N,N-di(1–4C)alkylcarbomoyl(2–4C)alkynyl, such as N,N-dimethylcarbamoylethynyl, N,N-diethylcarbamoylethynyl, 3-(N,N-dimethylcarbamoyl)-1-propynyl, 3-(N,N-diethylcarbamoyl)-1-propynyl, 4-(N,N-dimethylcarbamoyl)-2-butynyl and 4-(N,N-diethylcarbamoyl)-2-butynyl;

for halogeno(2–6C)alkyl: halogeno(2–4C)alkyl, such as 2-chloroethyl, 2-bromoethyl, 2-fluoroethyl, dichloromethyl, difluoromethyl, 2,2,2-trifluoroethyl and pentafluoroethyl;

for (1–6C)alkoxy: (1–4C)alkoxy, such as methoxy, ethoxy, propoxy, isopropoxy and butoxy;

for di- or tri-halogeno(1–6C)alkoxy: di- or trihalogeno (1–4C)alkoxy, such as difluoromethoxy, trifluoromethoxy, 2,2,2-trifluoroethoxy, 3,3,3-trifluoropropoxy and pentafluoroethoxy;

for di- or trihalogeno(1–3C)alkoxy: difluoromethoxy, trifluoromethoxy and 2,2,2-trifluoroethoxy;

for (2–6C)alkenyloxy: (2–4C)alkenyloxy, such as vinyloxy, allyloxy, 1-propenyloxy and 2-butenyloxy;

for (1–4C)alkoxy(1–6C)alkyl: (1–2C)alkoxy(1–4C)alkyl, such as methoxymethyl, ethoxymethyl, 1-methoxyethyl, 2-methoxyethyl, 2-ethoxyethyl and 3-methoxypropyl;

for (1–4C)alkylthio(1–6C)alkyl: (1–2C)alkylthio(1–4C) alkyl, such as methylthiomethyl, 1-methylthioethyl, 2-methylthioethyl, 2-methylthioprop-2-yl, ethylthiomethyl, 1-ethylthioethyl, 2-ethylthioethyl and 2-ethylthioprop-2-yl;

for (1–4C)alkylsulphinyl(1–6C)alkyl: (1–2C)alkylsulphinyl (1–4C)alkyl, such as methylsulphinylmethyl, 1-methylsulphinyl, 2-(methylsulphinyl)ethyl, 2-(methylsulphinyl)prop-2-yl, ethylsulphinylmethyl, 1-(ethylsulphinyl)ethyl, 2-(ethylsulphinyl)ethyl and 2-(ethylsulphinyl)prop-2-yl;

for (1–4C)alkylsulphonyl(1–6C)alkyl: (1–2C) alkylsulphonyl(1–4C)alkyl, such as methylsulphonylmethyl, 1-(methylsulphonyl)ethyl, 2-(methylsulphonyl)ethyl, 2-(methylsulphonyl)prop-2-yl, ethylsulphonylmethyl, 1-(ethylsulphonyl)ethyl, 2-(ethylsulphonyl)ethyl and 2-(ethylsulphonyl)prop-2-yl;

for (1–4C)alkylenedioxy: methylenedioxy, ethylenedioxy and isopropylidenedioxy;

for (3–6C)cycloalkyl: cyclopropyl, cyclobutyl and cyclopentyl;

for (3–8C)cycloalkyl(1–6C)alkyl: (3–5C)cycloalkyl(1–2C) alkyl, such as cyclopropylmethyl, cyclopropylethyl, cyclobutylmethyl and cyclopentylmethyl;

for phenyl(1–6C)alkyl: phenyl(1–4C)alkyl, such as benzyl, 1-phenylethyl and 2-phenylethyl;

for phenyl(1–6C)alkoxy: phenyl(1–4C)alkoxy, such as benzyloxy, 1-phenylethoxy, 2-phenylethoxy, 2-phenylpropoxy and 3-phenylpropoxy;

for phenyl(1–3)alkoxy: benzyloxy, 1-phenylethoxy and 2-phenylethoxy;

for halogeno: fluoro, chloro, bromo and iodo;

for (1–6C)alkoxycarbonyl: (1–4C)alkoxycarbonyl, such as methoxycarbonyl, ethoxycarbonyl and propoxycarbonyl;

for (2–6C)alkenyloxycarbonyl: allyloxycarbonyl, 2-methyl-2-propenyloxycarbonyl and 3-methyl-3-butenyloxycarbonyl;

for phenyl(1–6C)alkoxycarbonyl: phenyl(1–4C)alkoxycarbonyl, such as benzyloxycarbonyl, 1-phenylethoxycarbonyl and 2-phenylethoxycarbonyl;

for (1–6C)alkanoyl: (1–4C)alkanoyl, such as formyl, acetyl and propionyl;

for (1–6C)alkylthio: (1–4C)alkylthio, such as methylthio and ethylthio;

for (1–6C)alkylsulphinyl: (1–4C)alkylsulphinyl, such as methylsulphinyl and ethylsulphinyl;

for (1–6C)alkylsulphonyl: (1–4C)alkylsulphonyl, such as methylsulphonyl] and ethylsulphonyl;

for (1–6C)alkanoylamino: (1–4C)alkanoylamino, such as formamido, acetamido and propionamido;

for N-[(1–4C)alkyl]trifluoroacetamide: N-methyltrifluoroacetamide and N-ethyltrifluoroacetamide;

for N-[(1–4C)alkyl]benzamido: N-methylbenzamido and N-ethylbenzamido;

for (1–4C)alkylcarbamoyl: N-methylcarbamoyl and N-ethylcarbamoyl;

for di(1–4C)alkylcarbamoyl: N,N-dimethylcarbamoyl and N,N-diethylcarbamoyl;

for N-(1–4C)alkylsulphamoyl: N-methylsulphamoyl and N-ethylsulphamoyl;

for N,N-di(1–4C)alkylsulphamoyl: N,N-dimethylsulphamoyl and N,N-diethylsulphamoyl;

for (1–6C)alkanesulphonamido: (1–4C) alkanesulphonamido, such as methanesulphonamido and ethanesulphonamido;

for 3-(1–6C)alkylureido: 3-(1–4C)alkylureido, such as 3-methylureido, 3-ethylureido and 3-propylureido; and for 3-(1–6C)alkylthioureido: 3-(1–4C)alkylthioureido, such as 3-methylthioureido, 3-ethylthioureido and 3-propylthioureido.

It will be appreciated that a term such as (1–6C)alkyl bearing a carboxy substituent is the same as carboxy(1–6C)alkyl.

A particular value for Ry and Rz includes, by way of example, for (1–6C)alkyl: (1–4C)alkyl, such as methyl, ethyl and propyl;

for (1–6C)alkyl bearing a carboxy, (1–6C)alkoxycarbonyl, carbamoyl, (1–6C)alkylcarbamoyl or di(1–6C) alkylcarbamoyl group:

(1–4C)alkyl bearing a carboxy, (1–4C)alkoxycarbonyl, carbamoyl, (1–4C)alkylcarbamoyl or di(1–4C) alkylcarbamoyl group, such as carboxymethyl, 1-(carboxy)ethyl, 2-(carboxy)ethyl, 2-(carboxy)propyl, methoxycarbonylmethyl, 1-(methoxycarbonyl)ethyl, 2-(methoxycarbonyl)ethyl, 1-(ethoxycarbonyl)ethyl, 2-(ethoxycarbonyl)ethyl, 2-(methoxycarbonyl)propyl, 2-(ethoxycarbonyl)propyl, carbamoylmethyl, 1-carbamoylethyl, 2-carbamoylethyl, 2-carbamoylpropyl, (N-methylcarbamoyl)methyl, (N-ethylcarbamoyl)methyl, 1-(N-methylcarbamoyl)ethyl, 2-(N-methylcarbamoyl)ethyl, 1-(N-ethylcarbamoyl)ethyl, 2-(N-ethylcarbamoyl)ethyl, 2-(N-methylcarbamoyl)ethyl, 1-(N-ethylcarbamoyl)ethyl, 2-(N-ethylcarbamoyl)ethyl, 2-(N-methylcarbamoyl)propyl, 2-(N-ethylcarbamoyl)propyl, (N,N-dimethylcarbamoyl)methyl, (N,N-diethylcarbamoyl)methyl, 1-(N,N-dimethylcarbamoyl)ethyl, 2-(N,N-dimethylcarbamoyl)ethyl, 1-(N,N-diethylcarbamoyl)ethyl, 2-(N,N-diethylcarbamoyl)ethyl, 2-(N,N-diethylcarbamoyl)ethyl, 2-(N,N-dimethylcarbamoyl)propyl and 2-(N,N-diethylcarbamoyl)propyl; and for phenyl(1–4C)alkyl: benzyl, 1-phenylethyl and 2-phenylethyl.

Particular values for Ra, Rc and Re include, for example, for halogeno: fluoro, chloro, bromo and iodo; for (1–4C) alkyl: methyl, ethyl and propyl; and for (1–4C)alkoxy: methoxy, ethoxy and propoxy.

Particular values for substituent Rb, Rd and Rf include, for example, chloro, bromo, iodo, methyl, ethyl, methoxy, ethoxy, trifluoromethyl and ethynyl.

A particular value for a substituent on a phenyl or benzene moiety of a substituent on Ar includes, by way of example, for (1–4C)alkyl: methyl and ethyl;

for (1–4C)alkoxy: methoxy and ethoxy; and for halogeno: fluoro, chloro, bromo and iodo.

Preferred values for Rb, Rd and Rf include, for example, methyl and halogeno (especially chloro or bromo). Preferred values for Ra, Rc and Re include, for example, methoxy.

A particular group of values for $R^1$ includes, for example, (1–6C)alkyl and (1–6C)alkoxy, each of which two groups bear a substituent selected from carboxy, (1–6C) alkoxycarbonyl, carbamoyl, N-(1–6C)alkylcarbamoyl and N,N-di(1–6C)alkylcarbamoyl.

A particular group of values for $R^3$ includes, for example, (1–6C)alkyl, (1–6C)alkoxy, (1–6C)alkylthio, (1–6C) alkylsulphinyl, (1–6C)alkylsulphonyl, halogeno, amino, N-(1–4C)alkylamino, N,N-di(1–4C)alkylamino, (2–6C) alkenyl, (2–6C)alkynyl, (1–6C)alkoxy(1–6C)alkyl, (1–6C) alkylthio(1–6C)alkyl, hydroxy(1–6C)alkyl, trifluoromethyl, trifluoromethoxy, carbamoyl, (1–4C)alkylcarbamoyl, di(1–4C)alkylcarbamoyl and (1–6C)alkoxycarbonyl. A particular sub-group of values for $R^3$ includes, for example, (1–4C)alkyl, (1–4C)alkoxy, (1–4C)alkylthio, halogeno, amino, N-(1–4C)alkylamino, N,N-di(1–4C)alkylamino, (1–4C)alkoxy(1–4C)alkyl, (1–4C)alkylthio(1–4C)alkyl and (1–4C)alkoxycarbonyl.

A particular sub-group of compounds of the invention includes, for example, compounds in which m and n are zero, 1 or 2, and more particularly n and m are zero or 1. A preferred value for n and m is zero.

A preferred group of compounds of the invention includes, for example, compounds in which $R^1$ is carboxy (1–4C)alkyl (such as 2-carboxypropyl or 2-carboxy-2-methylpropyl) and carboxy(1–4C)alkoxy (such as carboxymethoxy or 1-carboxyethoxy). Within this group, compounds in which m and n are zero are particularly preferred. $R^1$ is carboxy(1–4C)alkyl is particularly preferred.

Further independent sub-groups of compounds of the invention include, for example, compounds of the formula I in which:

(1) the group Het has partial structural formula IIa;
(2) the group Het has partial structural formula IIb;
(3) the group Het has partial structural formula IIc;
(4) the group Het has partial structural formula IId; and
(5) the group Het has partial structural formula IIe; and wherein, within each group, $R^1$, $R^2$, $R^3$, n, m and Ra to Rh have any of the values defined herein (including the particular and preferred values), and pharmaceutically acceptable salts thereof.

Within sub-groups (1), (2), (3), (4) and (5) a preferred group of compounds is that in which Het is a group of partial structural formula IIa, Ra is hydrogen, halogeno, (1–4C)alkyl or (1–4C)alkoxy; and Rb is hydrogen, halogeno, (1–4C)alkyl, methoxy, ethoxy, trifluoromethyl, trifluoromethoxy or ethynyl. An especially preferred group of compounds includes, for example, those compounds in which Ra is methoxy and Rb is methyl or halogeno. A particularly preferred value for Rb is, for example, methyl.

Compounds of the invention which are of particular interest include, for example, the specific embodiments set out hereinafter in the accompanying Examples. These compounds, or a pharmaceutically-acceptable salt thereof, are provided as a further feature of the invention.

Examples of metabolically labile ester derivatives of a carboxy group are esters formed with alcohols such as (1–6C)alkanols, for example methanol, ethanol, propanol and isopropanol; indanol; adamantol; (1–6C)alkanoyloxy (1–4C)alkanols such as pivaloyloxymethyl; glycolamides; (S-methyl-2-oxo-1,3-dioxol-4-yl)methyl alcohol; and (1–4C)alkyloxycarbonyl(1–4)alkanols.

Examples of metabolically labile amide derivatives of a carboxy group includes amides formed from ammonia and amines such as (1–4C)alkylamine, for example methylamine, di(1–4C)alkyl amines, (1–4C)alkoxy(1–4C) alkylamines such as methoxyethyl amine, phenyl(1–2C) alkylamines such as benzylamine; and amino acids such as glycine or an ester phenyl(1–2C)alkylamines such as benzylamine; and amino acids such as glycine or an ester It will be appreciated that where sub-groups of compounds of the invention, or particular or preferred groups of compounds of the invention or specific compounds of the invention are referred to, these groups include prodrugs of said compounds, such as metabolically labile esters or amides.

Suitable pharmaceutically-acceptable salts include, for example, salts with alkali metal (such as sodium, potassium or lithium), alkaline earth metals (such as calcium or magnesium), ammonium salts, and salts with organic bases affording physiologically acceptable cations, such as salts with methylamine, dimethylamine, trimethylamine, piperidine and morpholine. In addition, for those compounds which are sufficiently basic, suitable pharmaceutically-acceptable salts include, pharmaceutically-acceptable acid-addition salts with hydrogen halides, sulphuric acid, phosphoric acid and with organic acids such as citric acid, maleic acid, methanesulphonic acid and p-toluenesulphonic acid. Alternatively, the compounds of Formula I may exist in zwitterionic form.

The compounds of Formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise.

(a) A compound of the Formula III in which P is a protecting group, is deprotected.

A suitable protecting group P includes, for example, an (1–6C)alkoxycarbonyl group (such as methoxycarbonyl, ethoxycarbonyl or isobutoxycarbonyl), benzyloxycarbonyl (in which the benz ring may be optionally substituted, for example it may bear a halogeno, (1–4C)alkyl or (1–4C) alkoxy substituent), 2-methoxyethoxymethyl and tri(1–4C) alkylsilylethoxymethyl (such as 2-(trimethylsilyl) ethoxymethyl). A protecting group P may be removed from the compound of Formula III by treatment with one or more deprotecting agents. It will be appreciated that the deprotecting agent or agents will depend on the particular value for P. Suitable deprotecting agents and procedures for their use are well known in the art. For example, an alkoxycarbonyl group may be removed under basic conditions, such as sodium hydroxide or alkoxide (e.g. methoxide) in a suitable solvent such as methanol; a 2-methoxyethoxymethyl group may be removed using acidic conditions, such as hydrochloric acid in a suitable solvent such as ethanol; and a tri(1–4C) alkylsilylethoxymethyl group may be removed by using tetrabutylammonium fluoride in tetrahydrofuran, by using trifluoroacetic acid or by using a mixture of hydrochloric acid in a suitable solvent such as ethanol.

A compound of the Formula III may be obtained by coupling a compound of the Formula IV where T is bromo, iodo or trifluoromethanesulphonyloxy with a benzeneboronic acid of the formula IVa (or an anhydride or ester thereof) in the presence of a suitable base and in the presence of a palladium (O), palladium (II), nickel (O) or nickel (II) catalyst.

Suitable catalysts include, for example, tetrakis (triphenylphosphine)nickel(O), bis(triphenylphosphine) nickel(II)chloride, nickel(II)chloride, bis (triphenylphosphine) palladium(II)chloride, tetrakis (triphenylphosphine)palladium(O) and palladium(II) chloride.

A suitable base for use in the reaction is, for example, an alkali metal alkoxide such as sodium methoxide or sodium ethoxide, an alkali metal hydroxide such as sodium or potassium hydroxide, an alkali metal carbonate such as sodium or potassium carbonate, or an organic base such as tri(1–6C)alkylamine, for example, triethylamine.

The coupling is generally performed in the presence of a suitable solvent of diluent, for example, a hydrocarbon, such as toluene or xylene, an ether, such as dioxan or tetrahydrofuran, an (1–4C)alcohol such as methanol, ethanol or butanol, water, or mixtures thereof (for example, a mixture of toluene, ethanol and water).

The reaction is generally performed at a temperature in the range, for example, 50°–150° C., and conveniently at or about the reflux temperature of the solvent or mixture of solvents used.

Alternatively, the coupling of a compound of Formula IV with a benzeneboronic acid of formula IVa (or an anhydride or ester thereof) may be carried out using a source of fluoride ion under aqueous conditions, for example using potassium fluoride in a mixture of toluene and water under reflux.

Compounds of Formula IV may be obtained, for example, by reacting a sulphonyl halide of the Formula V wherein Hal is a halogeno group (such as chloro, bromo or iodo) with an appropriately protected amine of the Formula VI wherein P is a protecting group, for example under basic conditions using sodium hydride in N,N-dimethylformamide (DMF). Alternatively, a sulphonyl halide of the Formula V may be reacted with an amine of the Formula VII to give a compound of the Formula VIII which is then protected to give a compound of the Formula IV. The protecting group P is chosen so that it allows formation of the compound of formula III under the conditions described. Suitable protecting groups and procedures for use thereof are generally known in the art. The protection of an amine of formula VII or a compound of formula VIII may be carried out using standard procedures of organic chemistry. For example, an amine of the formula VII may be protected with an alkoxycarbonyl group or benzyloxycarbonyl group by reaction with the corresponding alkylchloroformate or benzylchloroformate in the presence of a base, such as a tertiary amine (for example pyridine or triethylamine), and in the presence of a solvent such as dichloromethane. A compound of the formula VIII may be protected on the sulphonamide nitrogen by a 2-methoxyethoxymethyl group or a trialkylsilylethoxymethyl group by reaction with 2-methoxyethoxymethyl chloride or trialkylsilylethoxymethyl chloride respectively, in the presence of a base such as diisopropylethylamine or sodium hydride, and in a suitable solvent such as DMF. Sulphonyl halides of Formula V are known in the art or may be obtained, for example, by analogy therewith, for example by analogy with the procedures described in European Patent applications, publication Nos. 558288 and 569193. A convenient method for obtaining sulphonyl halides of Formula V is from the corresponding amine of Formula IX. Amines of the Formula IX and VII are commercially available or are well known in the art, being described in standard works of heterocyclic chemistry, and others may be obtained by analogy therewith using standard procedures of organic chemistry. Benzeneboronic acids of the formula IVa (and their anhydride and esters) may also be obtained, for example, by conventional procedures of organic chemistry for obtaining such compounds or by analogy therewith, for example the procedures described in EPA 558288 and EPA 569193.

(b) An amine of the Formula VII (or an alkali metal salt thereof) is reacted with a sulphonyl halide of the Formula XI in which Hal. is a halogeno group (for example chloro, bromo or iodo) or a sulphonate of the Formula XIa in which Ri is an electron deficient phenyl group, for example 4-nitrophenyl, in a suitable solvent.

When a compound of Formula XI is used, a convenient solvent includes, for example, pyridine. A catalyst, such as 4-dimethylaminopyridine or 4-pyrrolidinopyridine, may be added to assist the coupling reaction. The reaction is generally carried out at a temperature in the range of, for example, 0° C. to 120° C. and more gen erally 20° C to 120° C. Alternatively a solvent such as dichloromethane, chloroform, dimethoxyethane, tetrahydrofuran, dioxan or DMF may be used in the presence of a suitable inorganic base, such as sodium or potassium carbonate (which may be present as an aqueous solution) or an organic base, for example a tertiary amine such as pyridine or triethylamine. When the alkali metal salt of the amine of Formula VII is used, this may be formed in situ, for example with the use of a suitable base such as lithium diisopropylamide at a temperature, for example, of about −60° C., or sodium hydride, for example, at ambient temperature, prior to the addition of the sulphonyl halide. It will be appreciated that the reaction of a sulphonyl halide with an amine to form a sulphonamide (and the type of solvents and conditions used therein) is well-known in the art.

When a compound of the Formula XIa is used, it is preferred to prepare the alkali metal salt of the amine of Formula VII in situ, as mentioned above, using, for example, DMF as solvent, prior to addition of the compound of Formula XIa. The reaction may then conveniently be carried out at or near ambient temperature. Sulphonyl halides of the formula XI may be obtained using procedures well known in the art, for example by analogy with the procedures used to obtain the compounds of formula V.

A compound of Formula XIa may be obtained using a similar procedure to that described above for the preparation of a compound of Formula III, but using a compound of Formula X in place of the compound of Formula IV. A compound of Formula X may be obtained by reaction of a sulphonyl halide of Formula V with the appropriate phenol of Formula Ri.OH, such as 4-nitrophenol, using conventional procedures, for example, by heating in pyridine or by using DMF as solvent in the presence of a tertiary amine, such as N,N-diisopropylethylamine, at a temperature in the range of, for example, 20°–100° C.

(c) A compound of the formula XII or XIIa in which P is a protecting group as defined hereinbefore and X is a functional group is reacted, using conventional techniques of organic chemistry, to convert the group X into a group $R^1$ (and the protecting group P if present is removed during or after functional group modification). As will be appreciated, a group $R^1$ may be obtained by chemical transformation of a variety of possible groups X in formulae XII and XIIa, and that the starting materials XII and XIIa may be obtained using analogous procedures is those described herein for the preparation of compounds of the formula I and III respectively, for example by a benzeneboronic acid of formula XIII in place of IVa. Standard textbooks of organic chemistry, such as Advanced Organic Chemistry editted by J. March (Wiley-Interscience), describe reactions suitable for the preparation of carboxyalkyl, carboxyalkenyl, carboxyalkynyl, carboxyalkoxy and carboxyalkylthio groups attached to an aromatic ring, (as present in the compounds of formula I and III), as well the esters and amides of such groups, and that one or more of these methods may be suitable for the preparation of compounds of the formula I or III. Suitable values for X include, but are not limited to, haloalkyl (such as bromomethyl), formyl, amino, halogeno, hydroxy and mercapto.

For example a compound of the formula XIIa in which X is bromomethyl may be alkylated with a suitable substituted malonic acid ester under basic conditions, followed by hydrolysis and decarboxylation to give a compound of the formula I in which $R^1$ is carboxyalkyl. As a further example, a compound of the formula XIIa in which X is hydroxy or mercapto may be alkylated with a halogenoalkyl ester (such as an alkylbromoacetate) under basic conditions, followed by hydrolysis, to give a compound of the formula I in which $R^1$ is carboxyalkoxy or carboxyalkylthio. Examples of process (c) are illustrated in the Examples hereinafter.

It will also be appreciated that a compound of the formula I may also be converted into another compound of formula I by conventional functional group interconversion.

It will be appreciated that, in addition to the protecting group P referred to above, it may be convenient or necessary to protect one or more functional groups with a suitable protecting group prior to carrying out the process of (a), (b) or (c) above, or prior to carrying out a functional group interconversion, followed by removal of the protecting group. Suitable protecting groups and procedures for their use, together with procedure for removing the protecting group, are well known in the art, for example as described in "Protective Groups in Organic Syntheses" by Theodora Greene (John Wiley and Sons Inc., 1981).

Whereafter, when a pharmaceutically-acceptable salt of a compound of formula I is required, it may be obtained, for example, by reaction with the appropriate base affording a physiologically-acceptable cation, or with the appropriate acid affording a physiologically-acceptable amine, or by any other conventional salt formation procedure.

Additionally, a compound of the formula I may be convened into a prodrug (for example, a metabolically labile ester or amide) by methods well known in the art. For example, a pharmaceutically acceptable metabolically labile ester or amide may be formed respectively by esterifying a compound of the formula I bearing a carboxylic acid (or hydroxy) group or reacting the carboxylic acid group (or a reactive derivative thereof) with the appropriate amine, using conventional techniques.

Further, when an optically active form of a compound of formula I is required, one of the aforesaid processes may be carried out using an optically active starting material. Alternatively, the racemic form of a compound of formula I may be resolved, for example by reaction with a optically active form of a suitable organic base, for example, ephedrine, $\underline{N},\underline{N},\underline{N}$-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure, for example using an aqueous mineral acid such as dilute hydrochloric acid.

Certain of the intermediates defined or exemplified herein are novel, for example, compounds of the formula III, XII and XIIa, and are provided as a further feature of the invention.

As stated above, the compounds of formula I will have beneficial pharmacological effects in warm-blooded animals (including man) in diseases and medical conditions where elevated or abnormal levels of endothelin play a significant causative role. (References to studies supporting the implication of endothelin in various diseases or medical conditions are, for example, disclosed in International Patent Applications, Publication Nos. WO 93/21219 and WO 94/02474.) The compounds of the invention will thus be useful in the treatment of diseases or medical conditions such as hypertension, pulmonary hypertension, congestive heart failure, dyslipidaemia, atherosclerosis, restenosis, acute and chronic renal failure, ischaemic stroke, subarachnoid haemorrhage, intermittent claudication, critical limb ischaemia, asthma, and organ failure after general surgery or translantation. They may also be useful for the treatment of pre-eclampsia, premature labour, myocardial infarction, angina pectoris, dysrrhythmia, cardiogenic and endotoxin shock, diabetes mellitus, Raynaud's disease, scleroderma, Buerger's disease, systemic sclerosis, bronchitis, acute respiratory distress syndrome, liver cirrhosis, osteoporosis, Crohn's disease, ulcerative colitis, irritable bowel syndrome, urinary incontinence, migraine, glaucoma, arthritis and certain cancers.

The endothelin receptor antagonist activity of the compounds of the invention may be assessed using one or more of the following procedures:

Test A:

The endothelin receptor antagonist activity of compounds of formula I may be assessed in vitro by their ability to inhibit binding of $[^{125}I]$-Endothelin-1 to its receptors. Human $ET_A$ or $ET_B$ receptors (sub-types of the endothelin receptor) were expressed in Mouse Erythroleukemic Cells (MEL cells) by using standard molecular techniques (for example, as described by Sambrook J., Fritsch E. F. & Maniatis T. (1989) Molecular Cloning: A Laboratory Manual, 2nd Edition, Cold Spring Harbor Press, USA). cDNA sequences encoding the human $ET_A$ and $ET_B$ receptor (Hosoda K. et al (1991), FEBS Lett., 287, 23–26 and Sakamoto A. et al, (1991), Biochem. Biophys Res. Comm., 178, 656–663) are subcloned into pBluescript vector followed by insertion into the MEL cell expression vector pEV as described by Needham et al (1992), Nuc. Acids Res., 20, 997–1003. The resultant expression vector was transfected into MEL cells by electroporation using procedures described by Shelton et at., (1993), Receptors and Channels, 1, 25–37. MEL cells expressing the recombinant human $ET_A$ or $ET_B$ receptor were grown in Dulbecco's Modified Eagle's Medium (DMEM) with 10% Fetal Calf Serum (FCS), 1% glutamine, 1% penicillin/streptomycin and 2 mg/ml Gibco Geneticin (G-418) sulphate. After 3–6 days induction with 1% $\underline{N}$, $\underline{N}$-dimethylsuphoxide, the MEL cells were harvested for membrane preparation. Freshly prepared MEL cell pellets ($3\times10^9$ cells) were homogenised in 30 ml of buffer containing 50 mM 2-amino-2-(hydroxymethyl)-1,3-propanediol hydrochloride (Tris HCl), 0.19M sucrose, 5 µg/ml soybean trypsin inhibitor, 100 µg/ml bacitracin, 1 mM benzamidine and 1 mM phenanthroline pH 7.4 at 5° C. Unbroken cells and nuclei were sedimented by centrifuging the homogenate at 1500× x g for 15 minutes at 5° C. The membrane pellet was resuspended in buffer and stored in liquid nitrogen until use.

$[^{125}I]$-Endothelin-1 binding to MEL cell membranes was measured in incubation buffer containing 50 mM Tris HCl, 1 mM $CaCl_2$, 0.05% polyoxyethylenesorbitan monolaurate, 0.1% Bovine Serum Albumin (BSA), 0.02% sodium azide pH 7.4 at 30° C. after 180 minutes incubation. Membrane suspension (equivalent to 1.5 µg and 0.5 µg protein/tube $ET_A$ and $ET_B$ receptor respectively) was added to the incubation containing test compound and 30pM$[^{125}I]$-Endothelin-1 in a total volume of 225 µl. Nonspecific binding was measured in the presence of 100 nM unlabelled Endothelin-1. The incubation was terminated by harvesting the incubation with 50 mM Tris pH 7.4 through a GF/B filter on a Brandel cell harvestor. The filter discs were punched out and counted in a gamma counter. Compounds are tested in triplicate over a range of concentrations and $IC_{50}$ (or $pIC_{50}$) values calculated.

In general, compounds of formula I as defined above show inhibition in Test A with a $pIC_{50}$ of 6 or more.

Test B:

The endothelin receptor antagonist activity of compounds of formula I may be assessed in vitro in isolated tissues by their ability to inhibit the relaxant response to endothelin-1 in the guinea-pig isolated taenia coli. Guinea pigs of either sex and weight >250 g are killed by cervical dislocation and the caecum removed and placed in cold oxygenated Krebs solution. Strips of taenia coli are dissected out and approximately 4 cm lengths set up for isotonic recording in a 20 ml organ bath containing oxygenated Krebs solution at 32° C. After a 90–120 minute equilibration period to allow the tissue to spontaneously develop an increased tone, a cumulative concentration-response curve (relaxation) is constructed to endothelin-1 (0.3–10 nM). The tissue is then washed for a period of at least 90 minutes before construction of a second concentration-response curve to endothelin-1 in the presence of the test compound. The test compound is added to the organ bath (at an initial concentration of 20 µM) at least 30 minutes before constructing the second concentration-response curve to endothelin-1. The endothelin-1 concentration ratio for each experiment is determined by comparing the most parallel portions of the control and drug treated concentration-response curves. From this a $pA_2$ is calculated: $pA_2 = -\log[\text{molar drug concentration}] + \log[\text{concentration ratio} -1]$.

Test C:

This in vivo test involves the measurement of the antagonist effect of the test compound against the pressor response induced by intravenously-administered proendothelin-1 in a pithed rat preparation.

Male rats (280–330 g) are anaesthetised with halothane and artificially respired through a tracheal cannula. Rats are pithed by passing a 2 mm diameter needle through the orbit, through the foramen magnum, and down into the spinal canal. The left femoral vein and the right carotid artery are isolated and catheters filled with heparinised saline are implanted for administration of compounds and measurement of blood pressure respectively. Body temperature is maintained at 38° C. (as measured rectally) by a heated pad. Rats with an initial baseline mean arterial pressure of less than 55 mmHg or greater than 70 mmHg are excluded. Blood pressure is allowed to stabilize for approximately 10 minutes before a baseline reading is taken. Two initial challenges of proendothelin-1 (0.3 and 1.0 nmol kg$^{-1}$) are administered intravenously in a cumulative fashion and pressor responses recorded. Thereafter, a 55 minute recovery period is allowed and rats in which the blood pressure fails to return to within 20% of the baseline are excluded. Test compound is dosed intravenously at a dose volume of 1.0 ml kg$^{-1}$ body weight and further challenges of proendothelin-1 are administered 5 minutes later. Proendothelin-1 is administered cumulatively in increasing doses (starting at 0.3 nmolkg-) until pressor responses are observed. Endothelin receptor antagonism is quantified by calculating dose ratio shifts at the 30 mmHg change level.

Test D:

This in vivo test involves the measurement of the antagonist effect of the test compound against the pressor response induced by intravenously-administered proendothelin-1 in a conscious rat preparation.

Male rats (260–290 g) are anaesthetised with Saffan administered via the tail vein. The right jugular vein and carotid artery are isolated and catheters filled with heparin implanted. These are exteriorised at the back of the neck using a metal trochar and the neck incision closed with autoclips. Rats are housed individually with free access to food and water during the recovery phase. Later in the day, food is removed and the rats are fasted overnight with free access to water. The following day the rats are placed in perspex restraining tubes and the arterial catheter drained and connected to a pressure transducer for measurement of mean arterial pressure. Following a ten minute stabilization period, proendothelin-1 (usually 0.3–1.0 nmol kg-$^1$) is administered cumulatively until a pressor response of 30 mmHg is achieved. The animals are then returned to their cages and allowed to recover for 2 hours. The test compound is administered orally (by gavage) at a known time point during the recovery period. The dose response curve to proendothelin-1 is then repeated at a fixed time after the oral dose (usually 0.5 or 1.0 hours) and again at a further time point (3 or 5 hours). Endothelin receptor antagonism is quantified by calculating dose ratio shifts at the 30 mmHg change level.

By way of illustration of the endothelin antagonist properties of compounds of the formula I, the compound of Example 1 showed a $pIC_{50}$ value of 8.3 in Test A.

The compounds of formula I will generally be administered for therapeutic or prophylactic purposes to warm-blooded animals (including man) requiring such treatment in the form of a pharmaceutical composition, as is well known in the pharmaceutical art. According to a further feature of the invention there is provided a pharmaceutical composition comprising a compound of formula I, or a pharmaceutically acceptable salt thereof as defined above, together with a pharmaceutically acceptable diluent or carrier. Such compositions will conveniently be in a form suitable for oral administration (e.g. as a tablet, capsule, solution, suspension or emulsion) or parenteral administration (e.g. as an injectable aqueous or oily solution, or injectable emulsion).

The compounds of formula I, or a pharmaceutically acceptable salt thereof, may also be advantageously administered for therapeutic or prophylactic purposes together with another pharmacological agent known in the general art to be of value in treating one or more of the diseases or medical conditions referred to hereinabove, such as beta-adrenergic blocker (for example atenolol), a calcium channel blocker (for example nifedipine), an angiotensin converting enzyme (ACE) inhibitor (for example lisinopril), a diuretic (for example furosemide or hydrochlorothiazide), an endothelin converting enzyme (ECE) inhibitor (for example phosphoramidon), a neutral endopeptidase (NEP) inhibitor, an HMGCoA reductase inhibitor, a nitric oxide donor, an anti-oxidant, a vasodilator, a dopamine agonist, a neuroprotective agent, asteroid, a beta-agonist, an anti-coagulant, or a thrombolytic agent. It is to be understood that such combination therapy constitutes a further aspect of the invention.

In general a compound of formula I (or a pharmaceutically acceptable salt thereof as appropriate) will be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will be administered in an analogous amount and manner to those described above for administration to humans. The compounds of formula I are also of value as pharmacological tools in the development and standardisation of test systems for the evaluation of the effects of endothelin in laboratory animals such as cats, dogs, rabbits, monkeys, rats and mice, as part of the continuing search for new and improved therapeutic agents.

The invention will now be illustrated by the following non-limiting Examples in which, unless otherwise stated:

(i) concentrations and evaporations were carried out by rotary evaporation in vacuo;

(ii) operations were carried out at room temperature, that is in the range 18°–26° C.;

(iii) chromatography and flash column chromatography was performed on Merck Kieselgel 60 (Art. no. 9385) and thin layer chromatography (TLC) was performed on 0.2 mm thickness plates of Kieselgel 60 (Art. no. 5717) obtained from E Merck, Darmstadt, Germany;

(iv) where a silica gel Mega Bond Elut column is referred to, this means (unless otherwise stated) a column containing 10 g of silica of 40 micron particle size, the silica being contained in a 60 ml disposable syringe and supported by a porous disc, obtained from Varian, Harbor City, Calif., USA under the name "Mega Bond Elut SI";

(v) yields, where given, are intended for the assistance of the reader only and are not necessarily the maximum attainable by diligent process development; and (vi) $^1$H NMR spectra were normally determined at 250 MHz in $d_6$-dimethylsulphoxide ($d_6$-DMSO) or CDCl$_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet; dd, doublet of doublets; dt, doublet of triplets.

EXAMPLE 1

Potassium ethyl methylmalonate (87 mg) was added to dry tetrahydrofuran (THF; 3 ml) under an argon atmosphere and the suspension cooled to 0° C. A 1.22M solution of n-butyl lithium in n-hexane (0.39 ml) was added over a 10 minute period and the mixture was stirred for 20 minutes. A solution of 4'-bromomethyl-N-(isobutoxycarbonyl)-N-(3-methoxy-5-methylpyrazin-2-yl)-2-biphenylsulphonamide (230 mg) dissolved in dry THF (3 ml) was added over a period of 10 minutes. The mixture was allowed to attain ambient temperature and stirring was continued for 1 hour and then it was heated to 50° C. for 30 minutes. The solvent was removed by evaporation and the residue was acidified to pH 2 by the addition of 2M hydrochloric acid. The aqueous phase was extracted with ethyl acetate (3×25 ml) and the combined organic extracts were evaporated to dryness. The residue was purified by chromatography through a Mega Bond Elut column (5 g), eluting first with 10% ethyl acetate in iso-hexane and then 50% ethyl acetate in iso-hexane. Combination of the later fractions containing the required product and evaporation of the solvent gave a gum (51 mg). A portion of this material (20 mg) was suspended in diphenyl ether (0.5 ml) and heated under reflux for 20 minutes. The reaction mixture was diluted with iso-hexane (0.5 ml) and applied to a Mega Bond Elut column (5 g) and eluted with iso-hexane. After removal of all the diphenyl ether, the eluent was changed to ether and the product fractions were collected and combined. The solvent was removed by evaporation and the residue dissolved in ethanol (1.5 ml) containing 5M sodium hydroxide solution (0.04 ml). The mixture was heated under reflux for 2 hours and then cooled. 2M hydrochloric acid (0.1 ml) was added and the solvent was removed by evaporation. The residue was triturated with diethyl ether (10 ml) and filtered. The filtrate was extracted with a saturated aqueous solution of sodium bicarbonate (3×5 ml) and the combined aqueous extracts were acidified to pH2 with 2M HCl. The mixture was extracted with diethyl ether (3×10 ml) and the combined organic extracts were dried (MgSO$_4$) and evaporated to give 4'-(2-carboxypropyl)-N-(3-methoxy-5-methylpyrazin-2-yl)-2-biphenylsulphonamide (12.3 mg); $^1$H NMR ($d_6$-DMSO): 1.23 (d, 3H), 2.43 (s, 3H), 2.74–2.93 (m, 2H), 3.05–3.25 (m, 1H), 4.0 (s, 3H), 7.32 (br s, 4H), 7.44 (dd, 1H), 7.68–7.85 (m, 2H), 8.24 (dd, 1H); mass spectrum ((positive electrospray (+ve ESP)): 442 (M+H)$^+$. The starting material potassium ethyl methylmalonate was obtained as follows: Potassium hydroxide (6.5 g) was dissolved in absolute ethanol (60 ml) and diethyl methylmalonate (20.3 g) was added in one portion. The reaction mixture was stirred at ambient temperature for 18 hours and heated under reflux for 30 minutes. The solvent was partially removed by evaporating to low volume (~20 ml) and diethyl ether (100 ml) was added. The precipitate which formed was removed by filtration and washed with diethyl ether (2×100 ml) to give potassium ethyl methylmalonate (15.7 g); $^1$H NMR ($d_6$-DMSO): 1.10–1.38 (m, 6H), 2.72 (q, 1H), 3.72–4.07 (m, 2H).

The starting material 4'-bromomethyl-N-(isobutoxycarbonyl)-N-(3-methoxy-5-methylpyrazin-2-yl)-2-biphenylsulphonamide was obtained as follows:

(i) A solution of bromine (0.11 ml) in chloroform (20 ml) was added dropwise over 20 minutes to a solution of 2-amino-5-methylpyrazine (0.218 g) in chloroform (30 ml) which was protected from light. The reaction mixture was stirred for 90 minutes after addition was complete and was then washed with water (50 ml). The organic phase was dried (MgSO$_4$) and volatile material was removed by evaporation to give a yellow oil. The oil was purified by elution with dichloromethane through a silica gel Mega Bond Elut column to give 2-amino-3-bromo-5-methylpyrazine (0.286 g) as white solid, m.p. 51°–52° C.; mass spectrum (positive chemical ionisation (+ve CI)): 188 (M+H)$^+$.

(ii) 2-Amino-3-bromo-5-methylpyrazine (0.374 g) was added to a freshly prepared solution of sodium methoxide in methanol (made by addition of sodium (0.115 g) to methanol (6 ml). The reaction mixture was heated under reflux for 18 hours, cooled to ambient temperature and the solvent removed by evaporation. Water (5 ml) was added to the residue and extracted with dichloromethane (3×20 ml). The combined organic extracts were dried (MgSO$_4$) and the solvent removed by evaporation. The residue was purified by chromatography on silica gel, eluting with dichloromethane to give 2-amino-3-methoxy-5-methylpyrazine as a white crystalline solid (0.208 g, 75%), m.p. 67°–69° C.; mass spectrum (+ve CI): 140 (M+H)$^+$.

(iii) 2-Iodobenzenesulphonyl chloride (obtained as described in *J Org Chem*, (1977), 42, 3265) (12.1 g) was added to a solution of 2-amino-3-methoxy-5-methylpyrazine (5.6 g) in pyridine (100 ml) and the solution was heated at 70° C. for 8 hours. Volatile material was removed by evaporation and water (200 ml) was added to the residue. The mixture was extracted with ethyl acetate (2×200 ml) and the extracts were washed with 2M hydrochloric acid (200 ml) and water (200 ml). The extracts were dried (MgSO$_4$) and the solvent was removed by evaporation. The residue was triturated with ether to give 2-iodo-N-(3-methoxy-5-methylpyrazin-2-yl)benzenesulphonamide (7.2 g), m.p. 136°–138° C.; $^1$H NMR ($d_6$-DMSO): 2.3 (s, 3H), 3.9 (s, 3H), 7.3(dt, 1H), 7.5–7.65 (m, 2H), 8.05–8.15 (m, 2H), 10.7–10.8 (br s, 1H).

(iv) Isobutyl chloroformate was added dropwise to a stirred solution of 2-iodo-N-(3-methoxy-5-methylpyrazin-2-yl)benzenesulphonamide (1.65 g), triethylamine (0.57 ml) and pyridine (0.16 ml) in dichloromethane (30 ml) under an atmosphere of argon. The mixture was stirred for 2 hours and then 2M hydrochloric acid (20 ml) was added. The organic layer was separated, washed with water (20 ml) and saturated sodium chloride solution and dried (MgSO$_4$). Volatile material was removed by evaporation and the residue was purified by flash chromatography, eluting with ethyl acetate/hexane (1:4 v/v), to give 2-iodo-N-(isobutoxycarbonyl)-N-(3-methoxy-5-methylpyrazin-2-yl)benzenesulphonamide (2.0 g) as a gum; $^1$H NMR (d$_6$-DMSO): 0.7 (d, 2H), 1.6–1.8 (m, 1H), 2.5 (s, 3H), 3.9 (d, 2H), (dd, 1H), 8.35 (dd, 1H). 4.0 (s, 3H), 7.4 (dt, 1H), 7.7 (dr, 1H), 8.15 (s, 1H), 8.2 (dd, 1H), 8.35 (dd, 1H).

(v) A mixture of 2-iodo-N-(isobutoxycarbonyl)-N-(3-methoxy-5-methylpyrazin-2-yl) benzenesulphonamide (252 mg), 4-methylbenzeneboronic acid (68 mg), tetrakis(triphenylphosphine)palladium(O) (11.5 mg), toluene (2.5 ml), ethanol (1.25 ml) and 2M sodium carbonate solution (3.75 ml) was stirred virorously and heated under reflux for 2 hours under an atmosphere or argon. Water (10 ml) was added and the mixture was extracted with ethyl acetate (2×10 ml). The extracts were washed with saturated sodium chloride solution (25 ml) and dried (MgSO$_4$). Volatile material was removed by evaporation and the residue was purified by flash chromatography, eluting with ethyl acetate/hexane (1:4 v/v), to give N-(isobutoxycarbonyl)-N-(3-methoxy-5-methylpyrazin-2-yl)-4'-methyl-2-1-biphenylsulphonamide (182mg); NMR (d$_6$-DMSO): 0.6 (d, 6H), 1.55–1.75 (m, 1H), 2.35 (s, 3H), 2.5 (s, 3H), 3.85 (d, 2H), 3.95 (s, 3H), 7.15–7.45 (m, 1H) 7.7–7.8 (m, 2H), 8.15 (s, 1H), 8.45–8.55 (m, 1H), mass spectrum (positive fast atom bombardment (+ve FAB), methanol/m-nitrobenzyl alcohol (NBA)): 470 (M+H)$^+$.

(vi) Azobis(isobutyronitrile) (150 mg) and N-bromosuccinimide (1.68 g) were added to a solution of N-(isobutoxycarbonyl)-N-(3-methoxy-5-methylpyrazin-2-yl)-4'-methyl-2-biphenylsulphonamide (4.44 g) in carbon tetrachloride (150 ml). The mixture was heated under reflux for 4 hours and then allowed to cool and filtered. The filtrate was concentrated by evaporation and the residue was purified by flash chromatography on silica (150 g), eluting with 20% ethyl acetate in isohexane. Fractions containing the product were combined and evaporated to give 4'-bromomethyl-N-(isobutoxycarbonyl)-N-(3-methoxy-5-methylpyrazin-2-yl)-2-biphenylsulphonamide (3.67 g); $^1$H NMR (d$_6$-DMSO): 0.6 (s, 6H), 1.6–1.7 (m, 1H), 3.8 (d, 2H), 3.95 (s, 3H), 4.8 (s, 2H), 7.3–7.5 (m, 5H), 7.7–7.8 (m, 2H), 8.15 (s, 1H), 8.45–8.55 (m, 1H); mass spectrum (+ve FAB, methanol/NBA): 548 (M+H)$^+$.

EXAMPLE 2

4'-Hydroxy-N-(isobutoxycarbonyl)-N-(3-methoxy-5-methylpyrazin-2-yl)-2-biphenylsulphonamide (0.5 g) was added to a solution of methyl bromoacetate (0.12 ml) in acetone (20 ml) containing potassium carbonate (0.166 g). The mixture was stirred for 18 hours and then heated under reflux for 1 hour and cooled. The solvent was removed by evaporation and water (20 ml) was added to the residue. The mixture was then extracted with ethyl acetate (2×20 ml). The combined organic extracts were washed successively with 2M sodium hydroxide solution (15 ml), water (20 ml) and brine (10 ml) and then dried (MgSO$_4$). The solvent was removed by evaporation and the residue was dissolved in dimethoxyethane (5 ml) and methanol (5 ml). 2M Sodium hydroxide solution (1 ml) was added and the mixture was stirred for 18 hours and evaporated to dryness. Water (20 ml) was added to the residue and the mixture was washed with ethyl acetate (2×15 ml). The aqueous phase was acidified to pH2 with 2M hydrochloric acid and extracted with ethyl acetate (3×15 ml). The combined organic phases were extracted with saturated aqueous sodium bicarbonate solution (2×15 ml) and the combined aqueous phase was acidified with 6M hydrochloric acid and extracted with ethyl acetate (3×15 ml). The combined organic extracts were washed with water (15 ml) and brine (15 ml) and dried (MgSO$_4$). The solvent was removed by evaporation and the residue crystallised from ether to give 4'-carboxymethoxy-N-(3-methoxy-5-methylpyrazin-2-yl)-2-biphenylsulphonamide (0.123 g) as a solid, m.p. 165°–166° C.; microanalysis found: C, 55.9; H, 4.5; N, 9.9%; C$_{20}$H$_{19}$N$_3$O$_6$S requires: C, 55.9; H, 4.46; N, 9.78%; $^1$H NMR (d$_6$-DMSO): 2.24 (s, 3H), 3.84 (s, 3H), 4.67 (s, 2H), 6.78–6.95 (m, 2H), 7.16 (d, 2H), 7.27 (d, 1H); 7.49–7.66 (m, 3H), 8.06 (d, 1H), 9.50 (br s, 1H); mass spectrum (–ve ESP): 428 (M–H)$^-$.

The starting material 4'-hydroxy-N-(isobutoxycarbonyl)-N-(3-methoxy-5-methylpyrazin-2-yl)-2-biphenylsulphonamide was obtained as follows:

A mixture of 2-iodo-N-(isobutoxycarbonyl)-N-(3-methoxy-5-methylpyrazin-2-yl) benzenesulphonamide (2.0 g), 4-(t-butyldimethylsilyloxy)benzeneboronic acid (1.0 g), prepared by the method described in GB 2276162, tetrakis(triphenylphosphine)palladium(O) (0.25 g), sodium carbonate (0.5 g), dimethoxyethane (10 ml) and water (10 ml) was stirred and heated under reflux for 18 hours. The mixture was allowed to cool and diluted with water (50 ml) and extracted with ethyl acetate (2×50 ml). The combined organic extracts were washed with 0.1M sodium hydroxide solution (50 ml) and water (50 ml) and dried (MgSO$_4$). The solvent was removed by evaporation and the residue purified by chromatography on a Mega Bond Elut column, eluting with 25% ethyl acetate in hexane. Fractions containing the required product were combined and evaporated to dryness to give 4'-hydroxy-N-(isobutoxycarbonyl)-N-(3-methoxy-5-methylpyrazin-2-yl)-2-biphenylsulphonamide as a solid (0.85g); $^1$H NMR (CDCl$_3$): 0.7 (d, 6H), 1.59–1.79 (m, 1H), 2.49 (s, 3H), 3.83 (d, 2H), 3.96 (s, 3H), 5.15 (s, 1H), 6.78 (d, 2H), 7.24–7.38 (m, 3H), 7.50–7.59 (m, 2H), 7.91 (s, 1H), 8.57 (d, 1H); mass spectrum (+ve ESP): 472 (M+H)$^+$.

EXAMPLE 3

A solution of lithium hydroxide (498 mg) in water (10 ml) was added to a solution of N-(isobutoxycarbonyl)-4'-(1-methoxycarbonyl)ethoxy-N-(3-methoxy-5-methylpyrazin-2-yl)-2-biphenylsulphonamide (1.30 g) in tetrahydrofuran (25 ml) and methanol (10 ml) and the solution was stirred for 18 hours. Volatile material was removed by evaporation and the residue was dissolved in water (20 ml). The solution was acidified with 20% aqueous citric acid and extracted with ethyl acetate (2×25 ml). The extracts were re-extracted with saturated sodium bicarbonate solution (2×15 ml), cooled to 0° C. and acidified with 20% aqueous citric acid. The mixture wig extracted with ethyl acetate (2×25 ml) and the extracts were dried (MgSO$_4$). Volatile material was removed by evaporation and the residue was triturated with ether to give 4'-(1-carboxy)ethoxy-N-(3-methoxy-5-methylpyrazin-2-yl)2-biphenylsulphonamide (730 mg), m.p. 188°–190° C.; microanalysis found: C, 56.7; H, 4.9; N, 9.3%; C$_{21}$H$_{21}$N$_3$O$_6$S requires: C, 56.9; H, 4.8; N, 9.5%.

The starting N-(isobutoxycarbonyl)-4'-(1-methoxycarbonyl)ethoxy-N-(3-methoxy-5-methylpyrazin-2-yl)-2-biphenylsulphonamide was obtained as follows:

A mixture of 4'-hydroxy-N-(isobutoxycarbonyl)-N-(3-methoxy-5-methylpyrazin-2-yl)-2-biphenylsulphonamide (1.25 g), methyl-2-bromopropionate (576 mg) and potassium carbonate (440 mg) in acetone (25 ml) was heated under reflux for 18 hours. Volatile material was removed by evaporation and water (50 ml) was added to the residue. The mixture was extracted with dichloromethane (25 ml) and the extracts were washed with water (25 ml) and saturated sodium chloride solution (25 ml). The solution was dried (MgSO$_4$) and the solvent was removed by evaporation. The residue was purified by eluting with ethyl acetate/hexane (1:1 v/v) through a silica gel Mega Bond Elut column to give N-(isobutoxycarbonyl)-4'-(1-methoxycarbonyl)ethoxyl-N-(3-methoxy-5-methylpyrazin-2-yl)-2-biphenylsulphonamide as a gum; $^1$H NMR (DMSO-d$_6$): 0.6 (d, 6H), 1.5–1.7 (m, 4H), 2.5 (s, 3H), 3.7 (s, 3H), 3.8 (d, 2H), 4.0 (s, 3H), 5.0 (q, 1H), 6.9 (d, 2H), 7.3 (d, 2H), 7.4–7.5 (m, 1H), 7.7–7.8 (m, 2H), 8.15 (s, 1H), 8.45–8.5 (m, 1H).

EXAMPLE 4

Using an analogous procedure to that described in Example 3, but starting from N-(5-chloro-3-methoxypyrazin-2-yl)-N-(isobutoxycarbonyl)-4'-(1-methoxycarbonyl)ethoxy-2-biphenylsulphonamide, there was obtained in 55% yield 4'-(1-carboxy)ethoxy-N-(5-chloro-3-methoxypyrazin-2-yl)-2-biphenylsulphonamide, m.p. 223°–225° C.; $^1$H NMR (DMSO-d$_6$): 1.55 (d, 3H), 3.9 (s, 3H), 3.9 (s, 3H), 4.8 (q, 1H), 6.85 (d, 2H), 7.15 (d, 2H), 7.25 (d, 1H), 7.5–7.65 (m, 2H), 7.7 (s, 1H), 8.05 (d, 1H), 10.2 (s, 1H).

The starting N-(5-chloro-3-methoxypyrazin-2-yl)-N-(isobutoxycarbonyl)-4'-(1-methoxycarbonyl)ethoxy-2-biphenylsulphonamide was obtained as follows:

(i) Methyl 2-aminopyrazine-3-carboxylate (5.4 g) was suspended in glacial acetic acid (40 ml) and water (140 ml) was added. The mixture was warmed to 40° C. and chlorine gas was bubbled through it. The resulting clear solution was then cooled to 0° C. and chlorine addition continued for 20 minutes, at which time the weight of the reaction mixture had increased by 4.8 g. The precipitate which had formed was removed by filtration and the liquors were treated with chlorine for a further 10 minutes, whereby the weight increased by a further 2.2 g. A second precipitate was filtered off and the combined solids were stirred with a solution of sodium bisulphite (9 g) in water (60 ml) for 1.5 hours. The solid was filtered and washed with ice/water (2×100 ml) and dried (MgSO$_4$) to give methyl 2-amino-5-chloropyrazine-3-carboxylate (4.3 g); $^1$H NMR (d$_6$ DMSO): 3.87 (s, 3H), 7.5 (br s, 2H), 8.37 (s, 1H); mass spectrum (+ve CI): 188 (M+H)$^+$.

(ii) Methyl 2-amino-5-chloro-3-carboxylate (3.75 g) was added to a solution of sodium hydroxide (2.0 g) in water (20 ml) and heated under reflux for 1.5 hours. The reaction mixture was cooled to 0° C. and the precipitate filtered off. This solid was redissolved in water (60 ml) with heating and the solution was filtered and acidified to pH 2 with 2M hydrochloric acid. The precipitate was filtered and washed with ice/water (2×20 ml) and dried. The resulting solid was suspended in diphenyl ether (15 ml) and heated under reflux in an argon atmosphere for 15 minutes. The reaction mixture was cooled to ambient temperature and diluted with n-hexane (15 ml). The precipitate so formed was filtered and washed with n-hexane (3×25 ml) to give 2-amino-5-chloropyrazine (1.78 g); $^1$H NMR (d$_6$ DMSO): 6.55 (br s, 2H), 7.67 (d, 1H), 7.95 (d, 1H); mass spectrum (+ve CI): 130 (M+H)$^+$.

(iii) 2-Amino-5-chloropyrazine (1.7 g) was dissolved in chloroform (190 ml) and pyridine (1.3 ml) was added under an argon atmosphere. The flask and its contents were protected from light and a solution of bromine (0.7 ml) in chloroform (85 ml) was added over a period of 1 hour. After stirring for 2 hours more bromine (0.07 ml) in chloroform (8.5 ml) was added and, after stirring for 30 minutes, pyridine (0.2 ml) was added. The reaction mixture was stirred for a further 30 minutes then washed with water (50 ml) and the organic phase was separated. The solvent was removed by evaporation and the residue was purified by chromatography through a bed of silica (90 g), eluting with hexane (200 ml) followed by dichloromethane. Dichloromethane fractions containing the product were evaporated to give 2-amino-3-bromo-5-chloropyrazine (1.68 g); $^1$H NMR (d$_6$ DMSO): 6.94 (br s, 2H), 8.09 (s, 1H); mass spectrum (+ve CI): 208 (M+H)$^+$.

(iv) Sodium (2.82 g) was dissolved in dry methanol (50 ml) under argon and 2-amino-3-bromo-5-chloropyrazine (1.68 g) was added in small portions at ambient temperature with stirring. The resulting stirred solution was heated under reflux and an argon atmosphere for 4 hours. Water (10 ml) was added at ambient temperature and the solvent removed by evaporation. A further volume of water (10 ml) was added and the aqeous phase was extracted with dichloromethane (3×50 ml). Combined organic extracts were dried (MgSO$_4$) and evaporated to give 2-amino-5-chloro-3-methoxypyrazine (1.28 g), m.p. 102°–103° C.; $^1$H NMR (d$_6$ DMSO): 3.90 (s, 3H), 7.53 (s, 1H); mass spectrum (+ve CI): 160 (M+H)$^+$.

(v) Isobutyl chloroformate (4.1 g) was added to a solution of 2-amino-5-chloro-3-methoxypyrazine (4.8 g) and pyridine (2.37 g) in dichloromethane (50 ml). The solution was left to stand for 20 hours and then two further portions of isobutyl chloroformate (1.02 g) and pyridine (0.59 g) were added at 2 hour intervals. 2M hydrochloric acid (25 ml) was added and the organic layer was separated. The solution was washed with 2M hydrochloric acid (2×25 ml), water (25 ml) and saturated sodium chloride solution (25 ml) The solution was dried (MgSO$_4$) and volatile material was removed by evaporation. The residue was recrystallised from isohexane to give isobutyl N-(5-chloro-3-methoxypyrazin-2-yl)carbamate (6.15 g), m.p. 90°–91° C.; microanalysis found: C, 46.3; H, 5.5; N, 16.4%; C$_{10}$H$_{14}$C$_1$N$_3$O$_3$ requires: C, 46.3; H, 5.4; N, 16.2%.

(vi) Isobutyl N-(5-chloro-3-methoxypyrazin-2-yl)carbamate (3.34 g) was added to a stirred suspension of sodium hydride (60% dispersion in oil; 0.56 g) in dry N,N dimethylformamide (20 ml) at 0° C. The mixture was stirred at 0° C. for 1 hour and then a solution of 2-iodobenzenesulphonyl chloride (obtained as described in J Org Chem, 1977, 42, 3265) (4.68 g) was added. The mixture was stirred for 2 hours and then volatile material was removed by evaporation. The residue was dissolved in water (50 ml) and the solution was acidified with 20% aqueous citric acid and extracted with ethyl acetate (3×20 ml). The extracts were washed with water (25 ml) and saturated sodium chloride solution (25 ml) and dried (MgSO$_4$). Volatile material was removed by evaporation and the residue was purified by gradient elution with 10–35% ethyl acetate/isohexane through a silica gel Mega Bond Elut column to give N-(5-chloro-3-methoxypyrazin-2-yl)-N-(isobutoxycarbonyl)-2-iodobenzenesulphonamide (2.64 g); $^1$H NMR (d$_6$-DMSO): 0.67 (s, 6H), 1.65–1.8 (m, 1H), 3.9 (d, 2H), 4.0 (s, 3H), 3.9 (s, 3H), 7.4 (dd, 1H), 7.8 dd, 1H), 8.2 (d, 1H), 8.3 (d, 1H), 8.4 (s, 1H).

(vii) Using an analogous procedure to that described in Example 1 part (v), but starting from N-(5-chloro-3-methoxypyrazin-2-yl)-
N-(isobutoxycarbonyl)-2-iodobenzenesulphonamide and 4-(2-(2H)-tetrahydropyranyloxy)phenylboronic acid, there was obtained in 57% yield N-(5-chloro-3-methoxypyrazin-2-yl)-
N-(isobutoxycarbonyl)-4'-[2-(2
H)-tetrahydropyranyloxy]-2-biphenylsulphonamide, m.p. 142°–143° C.; microanalysis found: C, 56.3; H, 5.5; N, 7.1%; $C_{27}H_{30}C_1N_3O_7$ requires: C, 56.3; H, 5.25; N, 7.3%.

(vii) N-(5-Chloro-3-methoxypyrazin-2-yl)-
N-(isobutoxycarbonyl)-4'-[2-(2
H)-tetrahydropyranyloxy]-2-biphenylsulphonamide (1.15 g) and pyridinium-p-toluenesulphonate (50 mg) in ethanol (50 ml) was heated at 60° C. for 3 hours. Volatile material was removed by evaporation and the residue was triturated with ether/hexane (1:1 v/v) to give N-(5-chloro-3-methoxypyrazin-2-yl)-4'-hydroxy-
N-(isobutoxycarbonyl)-2-biphenylsulphonamide (0.96 g), m.p. 175°–177° C.; microanalysis found: C, 53.9; H, 4.8; N, 8.2%; $C_{21}H_{22}C_1N_3O_6$ requires: C, 53.7; H, 4.5; N, 8.5%.

(viii) Using an analogous procedure to that described in Example 3, but starting from N-(5-chloro-3-methoxypyrazin-2-yl)-4'-hydroxy-
N-(isobutoxycarbonyl)-2-biphenylsulphonamide, there was obtained in 26% yield N-(5-chloro-3-methoxypyrazin-2-yl)-
N-(isobutoxycarbonyl)-4'-(1-methoxycarbonyl)ethoxy-2-biphenylsulphonamide; mass spectrum (positive electrospray): 578 $(M+H)^+$.

The 4-(2-(2H)-tetrahydropyranyloxy)phenylboronic acid used in step (vii) was obtained as follows:

(a) A solution of 4-bromophenol (86.5 g), 3,4-dihydro-2H-pyran (46.2 g) and pyridinium-p-toluenesulphonate (1.25 g) in dichloromethane (500 ml) was stirred under argon for 24 hours. The solution was washed with 2M sodium hydroxide solution (200 ml) and water (2×200 ml) and then dried ($MgSO_4$). Volatile material was removed by evaporation and the residue was triturated with hexane to give 2-(4-bromophenoxy)-2H-tetrahydropyran (94.3 g), m.p. 51°–53° C.

(b) tert-Butyl lithium in pentane (1.7M, 200 ml) was added over 20 minutes to a solution of 2-(4-bromophenoxy)-2 H-tetrahydropyran (38.6 g) in dry tetrahydrofuran (450 ml) at −90° C. under argon. The solution was stirred at −90° C. for 30 minutes and then a solution of trimethyl borate (30 ml) in dry tetrahydrofuran (50 ml) was added over 15 minutes. The solution was stirred at −90° C. for 30 minutes and then allowed to warm to −30° C. Saturated ammonium chloride solution (100 ml) was added and the mixture was left to warm to room temperature. Water (100 ml) was added and the mixture was extracted with ether (2×250 ml). The extracts were washed with water (2×200 ml) and dried ($MgSO_4$). Volatile material was removed by evaporation and the residue was recrystallised from a mixture of ether and hexane to give 4-(2-(2 H)-tetrahydropyranyloxy)phenylboronic acid (23.4 g), m.p. 140°–142° C.

EXAMPLE 5

Using an analogous procedure to that described in Example 3, but starting from 4'-(2-carboxy-2-methylpropyl)-N-(isobutoxycarbonyl)-
N-(3-methoxy-5-methylpyrazin-2-yl)-2-biphenylsulphonamide, there was obtained in 26% yield 4'-(2-carboxy-2-methylpropyl)-
N-(3-methoxy-5-methylpyrazin-2-yl)-2-biphenylsulphonamide, m.p. 202°–204° C.; microanalysis found: C, 60.1; H, 5.5; N, 8.9%; $C_{23}H_{25}N_3O_5S$ requires: C, 60.6; H, 5.5; N, 9.2%.

The starting material 4'-(2-carboxy-2-methylpropyl)-N-(isobutyloxycarbonyl)-
N-(3-methoxy-5-methylpyrazin-2-yl)-2-biphenylsulphonamide was obtained as follows:

(i) A 1.25M solution of n-butyl lithium in hexane (32 ml) was cooled to 0° C. under an argon atmosphere and diisopropylamine (4.05 g; 5.24 ml) was added slowly. The resulting mixture was cooled to −70° C. and stirred while methyl isobutyrate (4.08 g; 4.58 ml) was added dropwise while maintaining the temperature at <−60° C. After a further 30 minutes at −70° C., a solution of 4-bromobenzyl bromide (10.0 g) in anhydrous tetrahydrofuran (20 ml) was added and the temperature was maintained at −70° C. for a further 1.5 hours. The reaction mixture was allowed to attain ambient temperature then heated to reflux for 18 hours. On cooling, the mixture was acidified with 8% aqueous citric acid and extracted with ethyl acetate (3×75 ml). Insoluble material at the interface was removed by filtration and the combined organic phase was washed with brine (20 ml), dried (Mg $SO_4$) and evaporated. The residue was subjected to vacuum flash chromatography on silica eluting with a gradient of 0–10% ethyl acetate in hexane to give 4-(2-methoxycarbonyl-2-methylpropyl)bromobenzene (7.79 g); $^1$H NMR ($d_6$-DMSO): 1.13 (s, 6H); 2.79 (s, 2H), 3.60 (s, 3H), 7.04 (m, 2H), 7.46 (d of t, 2H); mass spectrum $(CI^+)$: 272 $(M+H)^+$.

(ii) 4-(2-Methoxycarbonyl-2-methylpropyl)bromobenzene (7.79 g) was dissolved in methanol (60 ml) and 2M aqueous sodium hydroxide solution (30 ml) was added. The solution was heated to reflux for 2 hours then cooled. The volume was reduced to approximately 25 ml by evaporation and the residue extracted with ethyl acetate (15 ml) then acidified with 2M hydrochloric acid and re-extracted with ethyl acetate (3×25 ml). The combined organic extract of the acidified aqueous phase was dried ($MgSO_4$) and evaporated to give 4-(2-carboxy-2-methylpropyl)bromobenzene (6.1 g); $^1$H NMR ($d_6$-DMSO): 1.08 (s, 6H), 2.78 (s, 2H), 7.11 (m, 2H), 7.46 (m, 2H); mass spectrum $(CI^+)$ 256 $(M+H)^+$.

(iii) 4-(2-Carboxy-2-methylpropyl)bromobenzene (1.93 g) was dissolved in anhydrous tetrahydrofuran (20 ml) and cooled to −70° C. A 1.25M solution of n-butyl lithium in hexane (18 ml) was added dropwise with stirring under an argon atmosphere, such that the temperature did not exceed −65° C. After a further 20 minutes, trimethyl borate was slowly added at −65° C. and the reaction mixture was allowed to attain −15° C. The reaction was quenched by the addition of a saturated aqueous solution of ammonium chloride (50 ml) and the mixture acidified by the addition of 2M HCl. The organic phase was separated and the aqueous layer was extracted with ethyl acetate (2×50 ml). The combined organic phase was washed with saturated sodium chloride solution (15 ml) and evaporated and the residue was triturated with hexane to give 4-(2-carboxy-2-methylpropyl)benzeneboronic acid (1.2 g); $^1$H NMR (DMSO-$d_6$): 1.06 (s, 6H), 2.78 (s, 2H), 7.11 (d, 2H), 7.67 (d, 2H), 7.9 (br s, 2H), 12.2 (br s, 1H); mass spectrum (−ve ESP) 221 $(M-H)^-$.

(iv) A solution of sodium carbonate (2.86 g) in water (4 ml) was added to a soultion of 2-iodo-N-(isobutoxycarbonyl)-
N-(3-methoxy-5-methylpyrazin-2-yl)benzenesulphonamide (6.2 g), (2-carboxy-2-methylpropyl)

benzeneboronic acid (3.0 g) and tetrakis(triphenylphosphine)palladium(O) (235 mg) in toluene (30 ml) and ethanol (20 ml). The mixture was stirred vigorously and heated under reflux for 18 hours under an atmosphere of argon. Water (100 ml) and ethyl acetate (100 ml) were added and the organic layer was separated. The organic phase was extracted with saturated sodium bicarbonate solution (50 ml) and the aqueous phases were combined. The solution was acidifed with 6M hydrochloric acid and extracted with ethyl acetate (3×50 ml). The extracts were washed with water (50 ml) and saturated sodium chloride solution (50 ml) and then dried (MgSO$_4$). Volatile material was removed by evaporation and the residue was triturated with ether/hexane (1:1 v/v) to give 4'-(2-carboxy-2-methylpropyl)-N-(isobutoxycarbonyl)-N-(3-methoxy-5-methylpyrazin-2-yl)-2-biphenylsulphonamide (2.25 g); $^1$H NMR (d$_6$-DMSO): 0.6 (d, 6H), 1.1 (s, 6H), 1.5–1.7 (m, 1H), 2.52 (s, 3H), 2.85 (s, 2H), 3.8 (d, 2H), 3.95 (s, 3H), 7.15 (d, 2H), 7.25 (d, 2H), 7.3–7.4 (m, 1H), 7.7–7.8 (m, 2H), 8.15 (s, 1H), 8.5–8.6 (m, 1H), 12.3 (s, 1H).

EXAMPLE 6

(Note: all parts by weight)

The compounds of the invention may be administered for therapeutic or prophylactic use to warm-blooded animals such as man in the form of conventional pharmaceutical compositions, typical examples of which include the following:

| a) Capsule (for oral administration) | |
|---|---|
| Active ingredient* | 20 |
| Lactose powder | 578.5 |
| Magnesium stearate | 1.5 |
| b) Tablet (for oral administration) | |
| Active ingredient* | 50 |
| Microcrystalline cellulose | 400 |
| Starch (pregelatinised) | 47.5 |
| Magnesium stearate | 2.5 |
| c) Injectable Solution (for intravenous administration) | |
| Active ingredient* | 0.05–1.0 |
| Propylene glycol | 5.0 |
| Polyethylene glycol (300) | 3.0–5.0 |
| Purified water | to 100% |
| d) Injectable Suspension (for intramuscular administration) | |
| Active ingredient* | 0.05–1.0 |
| Methylcellulose | 0.5 |
| Tween 80 | 0.05 |
| Benzyl alcohol | 0.9 |
| Benzalkonium chloride | 0.1 |
| Purified water | to 100% |

Note: the active ingredient * may typically be an Example described hereinbefore or as a pharmaceutically acceptable salt. Tablets and capsules formulations may be coated in conventional manner in order to modify or sustain dissolution of the active ingredient. Thus, for example, they may be coated with a conventional enterically digestible coating.

Chemical Formulae

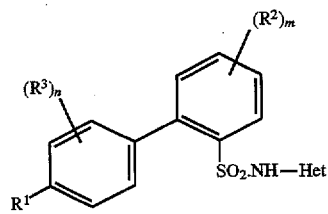
I

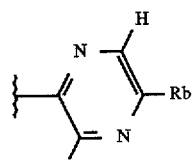
IIa

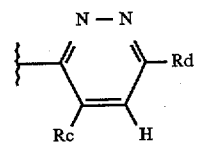
IIb

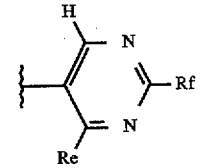
IIc

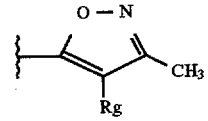
IId

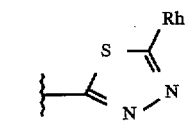
IIe

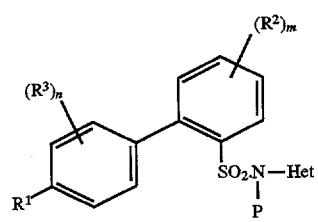
III

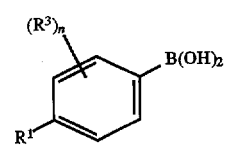
IVa

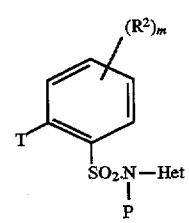
IV

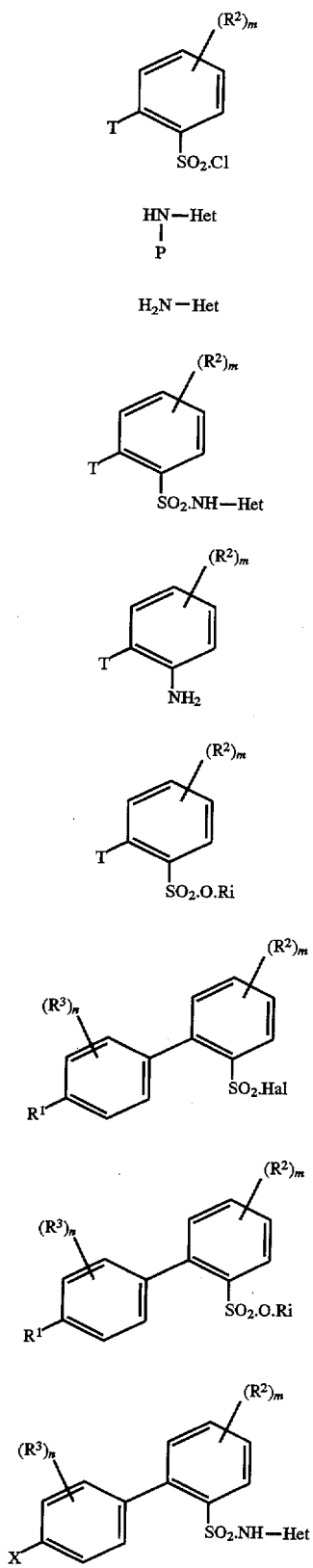
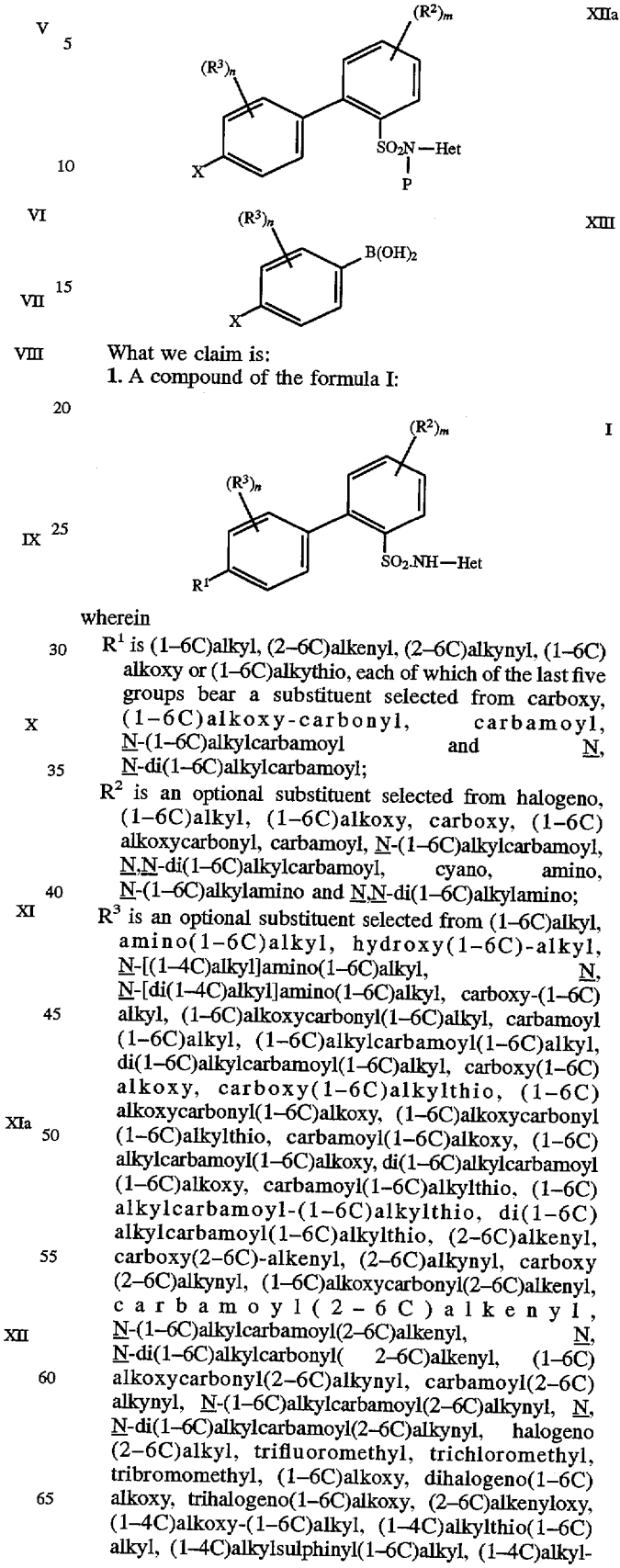

What we claim is:
1. A compound of the formula I:

wherein
R¹ is (1–6C)alkyl, (2–6C)alkenyl, (2–6C)alkynyl, (1–6C)alkoxy or (1–6C)alkylthio, each of which of the last five groups bear a substituent selected from carboxy, (1–6C)alkoxy-carbonyl, carbamoyl, $\underline{N}$-(1–6C)alkylcarbamoyl and $\underline{N},\underline{N}$-di(1–6C)alkylcarbamoyl;

R² is an optional substituent selected from halogeno, (1–6C)alkyl, (1–6C)alkoxy, carboxy, (1–6C)alkoxycarbonyl, carbamoyl, $\underline{N}$-(1–6C)alkylcarbamoyl, $\underline{N},\underline{N}$-di(1–6C)alkylcarbamoyl, cyano, amino, $\underline{N}$-(1–6C)alkylamino and $\underline{N},\underline{N}$-di(1–6C)alkylamino;

R³ is an optional substituent selected from (1–6C)alkyl, amino(1–6C)alkyl, hydroxy(1–6C)-alkyl, $\underline{N}$-[(1–4C)alkyl]amino(1–6C)alkyl, $\underline{N}$,$\underline{N}$-[di(1–4C)alkyl]amino(1–6C)alkyl, carboxy-(1–6C)alkyl, (1–6C)alkoxycarbonyl(1–6C)alkyl, carbamoyl(1–6C)alkyl, (1–6C)alkylcarbamoyl(1–6C)alkyl, di(1–6C)alkylcarbamoyl(1–6C)alkyl, carboxy(1–6C)alkoxy, carboxy(1–6C)alkylthio, (1–6C)alkoxycarbonyl(1–6C)alkoxy, (1–6C)alkoxycarbonyl(1–6C)alkylthio, carbamoyl(1–6C)alkoxy, (1–6C)alkylcarbamoyl(1–6C)alkoxy, di(1–6C)alkylcarbamoyl(1–6C)alkoxy, carbamoyl(1–6C)alkylthio, (1–6C)alkylcarbamoyl-(1–6C)alkylthio, di(1–6C)alkylcarbamoyl(1–6C)alkylthio, (2–6C)alkenyl, carboxy(2–6C)-alkenyl, (2–6C)alkynyl, carboxy(2–6C)alkynyl, (1–6C)alkoxycarbonyl(2–6C)alkenyl, carbamoyl(2–6C)alkenyl, $\underline{N}$-(1–6C)alkylcarbamoyl(2–6C)alkenyl, $\underline{N}$,$\underline{N}$-di(1–6C)alkylcarbonyl(2–6C)alkenyl, (1–6C)alkoxycarbonyl(2–6C)alkynyl, carbamoyl(2–6C)alkynyl, $\underline{N}$-(1–6C)alkylcarbamoyl(2–6C)alkynyl, $\underline{N}$,$\underline{N}$-di(1–6C)alkylcarbamoyl(2–6C)alkynyl, halogeno(2–6C)alkyl, trifluoromethyl, trichloromethyl, tribromomethyl, (1–6C)alkoxy, dihalogeno(1–6C)alkoxy, trihalogeno(1–6C)alkoxy, (2–6C)alkenyloxy, (1–4C)alkoxy-(1–6C)alkyl, (1–4C)alkylthio(1–6C)alkyl, (1–4C)alkylsulphinyl(1–6C)alkyl, (1–4C)alkylsulphonyl(1–6C)alkyl, (1–4C)alkylenedioxy, (3–6C) cycloalkyl, (3–8C)cycloalkyl(1–6C)alkyl, phenyl, phenyl(1–6C)alkyl, phenoxy, phenyl(1–6C)alkoxy, halogeno, hydroxy, mercapto, cyano, nitro, carboxy, (1–6C)alkoxycarbonyl, (2–6C)alkenyloxycarbonyl, phenyloxy-carbonyl, phenyl(1–6C)alkoxycarbonyl, (1–6C)alkanoyl, benzoyl, (1–6C)alkylthio, (1–6C) alkylsulphinyl, (1–6C)alkylsulphonyl, phenylthio, phenylsulphinyl, phenylsulphonyl, (1–6C) alkanoylamino, trifluoroacetyl, trifluoroacetamido, N-[(1–4C)alkyl]-trifluoroacetamido, benzamido, N-[(1–4C)alkyl]benzamido, carbamoyl, (1–4C)alkylcarbamoyl, di-(1–4C)alkylcarbamoyl, phenylcarbamoyl, sulphamoyl, N-(1–4C)alkyl-sulphamoyl, N,N-di(1–4C)alkylsulphamoyl, N-phenylsulphamoyl, (1–6C)alkane-sulphonamido, benzenesulphonamido, ureido, 3-(1–6C)alkylureido, 3-phenylureido, thioureido, 3-(1–6C)alkylthioureido, 3-phenylthioureido and a group —NRyRz in which Ry and Rz are independently selected from hydrogen, (1–6C)alkyl, phenyl(1–4C)alkyl and (1–6C)alkyl bearing a carboxy, (1–6C)alkoxycarbonyl, carbamoyl, (1–6C)alkylcarbamoyl or di(1–6C)alkylcarbamoyl group, or the group —NRyRz taken together complete a 1-pyrrolidinyl, 2-oxo-1-pyrrolidinyl, 1-piperidinyl or 2-oxo-1-piperidinyl ring;

Het is a heterocyclic ring of formula IIa:

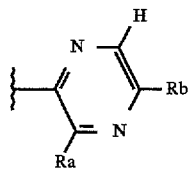

wherein Ra is selected from hydrogen, halogeno, (1–4C) alkyl, (1–4C)alkoxy and trifluoromethoxy; and Rb is selected from hydrogen, halogeno, (1–4C)alkyl, methoxy, ethoxy, trifluoromethyl and ethynyl;

m is zero, 1, 2 or 3;

n is zero, 1, 2 or 3;

and wherein any of said phenyl or benzene moieties of R may be unsubstituted or bear one or two substituents independently selected from (1–4C)alkyl, (1–4C)alkoxy, halogeno, cyano and trifluoromethyl; or a pharmaceutically-acceptable salt thereof.

2. A compound as claimed in claim 1 wherein n is zero; m is zero; and $R^1$ is selected from carboxymethyl, 1-carboxyethyl, 2-carboxyethyl, 2-carboxypropyl, methoxycarbonylmethyl, ethoxycarbonylmethyl, 1-(methoxycarbonyl)ethyl, 2-(methoxycarbonyl)ethyl, 1-(ethoxycarbonyl)ethyl, 2-(ethoxycarbonyl)ethyl, 2-(methoxycarbonyl)propyl, 2-(ethoxycarbonyl)propyl, carboxymethoxy, 1-carboxyethoxy, 2-carboxyethoxy, 2-carboxypropoxy, carboxymethylthio, 1-carboxyethylthio, 2-carboxyethylthio, 2-carboxypropylthio, methoxycarbonylmethoxy, ethoxycarbonylmethoxy, 1-(methoxycarbonyl)ethoxy, 1-(ethoxycarbonyl)ethoxy, 2-(methoxycarbonyl)ethoxy, 2-(ethoxycarbonyl)ethoxy, 2-(methoxycarbonyl)propoxy, 2-(ethoxycarbonyl)propoxy, (methoxycarbonyl)methylthio, ethoxycarbonylmethylthio, 1-(methoxycarbonyl)ethylthio, 1-(ethoxycarbonyl) ethylthio, 2-(methoxycarbonyl)ethylthio, 2-(ethoxycarbonyl)ethylthio, 2-(methoxycarbonyl) propylthio, 2-(ethoxycarbonyl)propylthio, carbamoylmethyl, 1-carbamoylethyl, 2-carbamoylethyl, 2-carbamoylpropyl, (N-methylcarbamoyl)methyl, (N-ethylcarbamoyl)methyl, 1-(N-methylcarbamoyl)ethyl, 2-(N-methylcarbamoyl)ethyl, 1-(N-ethylcarbamoyl)ethyl, 2-(N-ethylcarbamoyl)ethyl, 2-(N-methylcarbamoyl)ethyl, 1-(N-ethylcarbamoyl)ethyl, 2-(N-ethylcarbamoyl)ethyl, 2-(N-methylcarbamoyl)propyl, 2-(N-ethylcarbamoyl)propyl, (N,N-dimethylcarbamoyl)methyl, (N,N-diethylcarbamoyl)-methyl, 1-(N,N-dimethylcarbamoyl)ethyl, 2-(N,N-dimethylcarbamoyl)ethyl, 1-(N,N-diethylcarbamoyl)ethyl, 2-(N,N-diethylcarbamoyl)ethyl, 2-(N,N-dimethylcarbamoyl)propyl, 2-(N,N-diethylcarbamoyl)propyl, carbamoylmethoxy, 1-carbamoylethoxy, 2-carbamoyl-ethoxy, 2-carbamoylpropoxy, (N-methylcarbamoyl)methoxy, (N-ethylcarbamoyl)methoxy, 1-(N-methylcarbamoyl)-ethoxy, 2-(N-methylcarbamoyl)ethoxy, 1-(N-ethylcarbamoyl)-ethoxy, 2-(N-ethylcarbamoyl)-ethoxy, 2-(N-methylcarbamoyl)propoxy, 2-(N-ethyl-carbamoyl)propoxy, (N,N-dimethyl-carbamoyl)methoxy, (N,N-diethylcarbamoyl)methoxy, 1-(N,N-dimethylcarbamoyl)ethoxy, 2-(N,N-dimethylcarbamoyl)ethoxy, 1-(N,N-diethylcarbamoyl)ethoxy, 2-(N,N-diethyl-carbamoyl)ethoxy, 2-(N,N-dimethylcarbamoyl)propoxy, 2-(N,N-diethylcarbamoyl)propoxy, carbamoylmethylthio, 1-carbamoylethylthio, 2-carbamoylethylthio, 2-carbamoylpropylthio, (N-methylcarbamoyl)methylthio, (N-ethylcarbamoyl)methylthio, (N-ethylcarbamoyl)-methylthio, 1-(N-methylcarbamoyl)ethylthio, 2-(N-methylcarbamoyl)ethylthio, 1-(N-ethylcarbamoyl)-ethylthio, 2-(N-ethylcarbamoyl)ethylthio, 2-(N-methyl-carbamoyl)propylthio, 2-(N-ethylcarbamoyl)propylthio, (N,N-dimethylcarbamoyl)methylthio, (N,N-diethylcarbamoyl)methylthio, 1-(N,N-dimethylcarbamoyl)ethylthio, 2-(N,N-dimethylcarbamoyl)ethylthio, 1-(N,N-diethylcarbamoyl)ethylthio, 2-(N,N-diethylcarbamoyl)-ethylthio, 2-(N,N-dimethylcarbamoyl)propylthio, 2-(N,N-diethylcarbamoyl)propylthio, 2-carboxyethenyl, 3-carboxy-1-propenyl, 4-carboxy-2-butenyl, carboxyethynyl, 3-carboxy-1-propynyl, 4-carboxy-2-butynyl, 2-methoxycarbonylethenyl, 2-ethoxycarbonylethenyl, 3-methoxycarbonyl-1-propenyl, 3-ethoxycarbonyl-1-propenyl, 4-methoxycarbonyl-2-butenyl, 4-ethoxycarbonyl-2-butenyl, 2-carbamoylethenyl, 3-carbamoyl-1-propenyl, 4-carbamoyl-2-butenyl, 2-(N-methylcarbamoyl)ethenyl, 2-(N-ethylcarbamoyl)ethenyl, 3-(N-methyl-carbamoyl)-1-propenyl, 3-(N-ethyl-carbamoyl)-1-propenyl, 4-(N-methylcarbamoyl)-2-butenyl, 4-(N-ethyl-carbamoyl)-2-butenyl, 2-(N,N-dimethylcarbamoyl)ethenyl, 2-(N,N-diethyl-carbamoyl)ethyl, 3-(N,N-dimethylcarbamoyl)-1-propenyl, 3-(N,N-diethylcarbamoyl)-2-butenyl, 4-(N,N-dimethylcarbamoyl)-2-butenyl, 4-(N,N-diethylcarbamoyl)-2-butenyl, methoxycarbonylethynyl, ethoxycarbonylethynyl, 3-methoxycarbonyl-1-propynyl, 3-ethoxycarbonyl-1-propynyl, 4-methoxycarbonyl-2-butynyl, 4-ethoxycarbonyl-2-butynyl, carbamoylethynyl, 3-carbamoyl-1-propynyl and 4-carbamoyl-2-butynyl, N-methyl-carbamoylethynyl, N-ethylcarbamoylethynyl, 3-(N-methylcarbamoyl)-1-propynyl, 3-(N-ethylcarbamoyl)-1-propynyl, 4-(N-methyl-carbamoyl)-2-butynyl, 4-(N-ethylcarbamoyl)-2-butynyl, N,N-dimethylcarbamoylethynyl, N,N-diethylcarbamoylethynyl, 3-(N,N-dimethylcarbamoyl)-1-propynyl, 3-(N,N-diethyl-carbamoyl)-1-propynyl, 4-(N,N-dimethylcarbamoyl)-2-butynyl and 4-(N,N-diethyl-carbamoyl)-2-butynyl; or a pharmaceutically-acceptable salt thereof.

3. A compound as claimed is claim 1 wherein $R^1$ is selected from (1–6C)alkyl and (1–6C)alkoxy, each of which two groups bear a substituent selected from carboxy, (1–6C) alkoxycarbonyl, carbamoyl, N-(1–6C)alkylcarbamoyl and N,N-di(1–6C)alkylcarbamoyl; or a pharmaceutically-acceptable salt thereof.

4. A compound as claimed in claim 1 wherein $R^1$ is carboxy(1–4C)alkyl or carboxy(1–4C)alkoxy; or a pharmaceutically-acceptable salt thereof.

5. A compound as claimed in claim 1 wherein Ra is methoxy and Rb is methyl or halogeno.

6. A compound of the formula I as claimed in claim 1 selected from:

4'-(2-carboxypropyl)-N-(3-methoxy-5-methylpyrazin-2-yl)-2-biphenylsulphonamide,

4'-carboxymethoxy-N-(3-methoxy-5-methylpyrazin-2-yl)-2-biphenylsulphonamide,

4'-(1-carboxy)ethoxy-N-(3-methoxy-5-methylpyrazin-2-yl)-2-biphenylsulphonamide,

4'-(1-carboxy)ethoxy-N-(5-chloro-3-methoxypyrazin-2-yl)-2-biphenylsulphonamide and 4'-(2-carboxy-2-methylpropyl)-N-(3-methoxy-5-methylpyrazin-2-yl)-2-biphenylsulphonamide;

or a pharmaceutically-acceptable salt thereof.

7. A salt as claimed in claim 1 which is selected from salts with bases affording physiologically acceptable cations and, for those compounds of formula I which are sufficiently basic, salts with acids forming physiologically acceptable anions.

8. A pharmaceutical composition which comprises a compound of the formula I, or pharmaceutically acceptable salt thereof, as claimed in claim 1, together with a pharmaceutically-acceptable diluent or carrier.

9. A method of antagonising one or more of the actions of endothelin in a human or other warm-blooded animal requiring such treatment which comprises administering to said human or other warm-blooded animal an antagonistically effective amount of a compound of formula I, or a pharmaceutically-acceptable salt thereof, as claimed in claim 1.

* * * * *